(12) United States Patent
Tsusaka et al.

(10) Patent No.: US 10,098,701 B2
(45) Date of Patent: Oct. 16, 2018

(54) FORCE MEASUREMENT APPARATUS, FORCE MEASUREMENT METHOD, FORCE MEASUREMENT PROGRAM, FORCE MEASUREMENT INTEGRATED ELECTRONIC CIRCUIT, AND MASTER-SLAVE DEVICE

(71) Applicant: Panasonic Corporation, Osaka (JP)

(72) Inventors: Yuko Tsusaka, Osaka (JP); Yudai Fudaba, Osaka (JP); Jun Ozawa, Nara (JP)

(73) Assignee: Panasonic Intellectual Property Management Co., Ltd., Osaka (JP)

( * ) Notice: Subject to any disclaimer, the term of this patent is extended or adjusted under 35 U.S.C. 154(b) by 1149 days.

(21) Appl. No.: 14/021,253

(22) Filed: Sep. 9, 2013

(65) Prior Publication Data

US 2014/0171778 A1 Jun. 19, 2014

(30) Foreign Application Priority Data

Dec. 14, 2012 (JP) ................. 2012-273684

(51) Int. Cl.
*A61B 5/00* (2006.01)
*A61B 19/00* (2006.01)
*A61B 5/06* (2006.01)
*A61B 34/30* (2016.01)
*A61B 90/00* (2016.01)

(52) U.S. Cl.
CPC ............ *A61B 19/46* (2013.01); *A61B 5/06* (2013.01); *A61B 5/6843* (2013.01); *A61B 34/30* (2016.02); *A61B 90/06* (2016.02); *A61B 2090/065* (2016.02)

(58) Field of Classification Search
CPC ............ A61B 19/46; A61B 19/2203
See application file for complete search history.

(56) References Cited

U.S. PATENT DOCUMENTS

| 2009/0171371 A1* | 7/2009 | Nixon ............... A61B 34/30 606/130 |
| 2009/0248038 A1 | 10/2009 | Blumenkranz et al. |
| 2010/0094312 A1* | 4/2010 | Ruiz Morales ....... B25J 13/085 606/130 |

(Continued)

FOREIGN PATENT DOCUMENTS

| JP | 2009-527344 | 7/2009 |
| JP | 2010-507792 | 3/2010 |

(Continued)

*Primary Examiner* — Joseph M Santos Rodriguez
(74) *Attorney, Agent, or Firm* — Wenderoth, Lind & Ponack, L.L.P.

(57) ABSTRACT

A force measurement apparatus includes a force detection unit that measures a force generated when a forceps is brought into contact with an inside of a body when an operator inserts a forceps or an endoscope into the body and measures a force generated when the forceps acts on a living body from outside the body, a reference information generating unit that generates reference information serving as information of a force acquired by the force detection unit when the forceps is located at a predetermined position, and an individual force calculation unit that individually calculates a force generated when the forceps acts on the living body in the body based on the reference information.

11 Claims, 25 Drawing Sheets

(56) References Cited

U.S. PATENT DOCUMENTS

2012/0041436 A1 2/2012 Ullrich et al.

FOREIGN PATENT DOCUMENTS

| JP | 2011-517419 | 6/2011 |
| JP | 2012-040384 | 3/2012 |
| JP | 2012-235936 | 12/2012 |
| WO | 2007/098494 | 8/2007 |
| WO | 2008/049898 | 5/2008 |
| WO | 2012/153871 | 11/2012 |

* cited by examiner

*Fig.5*

| TIME (msec) | FORCE (N,Nm) | POSITION (m) | REFERENCE POINT | ID |
|---|---|---|---|---|
| $t_0$ | $f_0$ | $p_0$ | 1 | 1 |
| $t_{01}$ | $f_{01}$ | $p_{01}$ | 0 | 1 |
| .. | .. | .. | .. | .. |
| $t_1$ | $f_1$ | $p_1$ | 1 | 2 |
| $t_{11}$ | $f_{11}$ | $p_{11}$ | 0 | 2 |
| .. | .. | .. | .. | .. |
| $t_2$ | $f_2$ | $p_2$ | 1 | 3 |
| $t_{21}$ | $f_{21}$ | $p_{21}$ | 0 | 3 |
| ⋮ | ⋮ | ⋮ | ⋮ | ⋮ |

Fig.6

| TIME (msec) | FORCE (N,Nm) | POSITION (m) | ID OF REFERENCE INFORMATION | INDIVIDUAL FORCE |
|---|---|---|---|---|
| $t_0$ | $f_0$ | $p_0$ | 1 | $fr_0$ |
| $t_{01}$ | $f_{01}$ | $p_{01}$ | 1 | $fr_{01}$ |
| .. | .. | .. | .. | .. |
| $t_1$ | $f_1$ | $p_1$ | 20 | $fr_1$ |
| $t_{11}$ | $f_{11}$ | $p_{11}$ | 20 | $fr_{11}$ |
| .. | .. | .. | .. | .. |
| $t_2$ | $f_2$ | $p_2$ | 1 | $fr_2$ |
| $t_{21}$ | $f_{21}$ | $p_{21}$ | 1 | $fr_{21}$ |
| ⋮ | ⋮ | ⋮ | ⋮ | ⋮ |

Fig. 15

| TIME (msec) | FORCE (N,Nm) | POSITION (m) | REFERENCE POINT | ID | RE-CREATION FLAG |
|---|---|---|---|---|---|
| $t_0$ | $f_0$ | $p_0$ | 1 | 1 | 1 |
| $t_{01}$ | $f_{01}$ | $p_{01}$ | 0 | 1 | 1 |
| : | : | : | : | : | : |
| $t_1$ | $f_1$ | $p_1$ | 1 | 2 | 0 |
| $t_{11}$ | $f_{11}$ | $p_{11}$ | 0 | 2 | 0 |
| : | : | : | : | : | : |
| $t_2$ | $f_2$ | $p_2$ | 1 | 3 | 0 |
| $t_{21}$ | $f_{21}$ | $p_{21}$ | 0 | 3 | 0 |
| ..... | ..... | ..... | ..... | ..... | ..... |

FORCE MEASUREMENT APPARATUS, FORCE MEASUREMENT METHOD, FORCE MEASUREMENT PROGRAM, FORCE MEASUREMENT INTEGRATED ELECTRONIC CIRCUIT, AND MASTER-SLAVE DEVICE

BACKGROUND OF THE INVENTION

The technical field relates to a force measurement apparatus, a force measurement method, a force measurement program, a force measurement integrated electronic circuit, and a master-slave device, each of which measures a force acting when an operator inserts an instrument into a living body.

In recent years, endoscopic surgery is performed such that an operator fits a tube called a trocar in a hole formed in the abdomen of a human body, inserts a tip end of a surgical instrument such as a dedicated endoscope or forceps from the trocar into the body, and operates the forceps from outside the body while watching a video image of the endoscope displayed on a monitor screen.

SUMMARY OF THE INVENTION

The benefits of the endoscopic surgery, as compared to abdominal surgery, include less pain and less scarring. However, since an operator cannot directly touch an internal organ in the body, a force sense obtained when the forceps is brought into contact with an abdominal wall or the internal organ can be checked through the forceps by only the operator who grips the forceps, and cannot be quantitatively (numerically) checked.

In order to solve the above problem, a contact sensor is mounted on the tip end of a forceps, and a contact force at the tip end of the forceps is fed back to an operator that operates the forceps, so that a force acting on the tip end of the forceps can clearly be presented to the operator (see Unexamined Japanese Patent Publication No. 2012-40384 (Patent Literature 1)).

Alternatively, force sensors are disposed on an arm portion of a surgical robot and a surgical instrument, and a force acting on the tip end of a forceps or a robot arm is detected (see Japanese Translation of PCT Publication No. 2011-517419 (Patent Literature 2)).

However, in Patent Literature 1 and Patent Literature 2, since a contact sensor or a strain gauge is disposed at the tip end of a forceps or around the forceps, the contact sensor or the strain gauge need to be uneconomically attached in accordance with the shape or the size of the forceps. Furthermore, since the contact sensor and the strain gauge are brought into direct contact with an internal organ, a high sterilization level need to be maintained.

One non-limiting and exemplary embodiment provides a force measurement apparatus, a force measurement method, a force measurement program, and an force measurement integrated electronic circuit that can individually measure, in endoscopic surgery performed by inserting a surgical instrument such as a forceps or an endoscope into a human body, a force acting on the human body by the surgical instrument from outside the human body.

Another object of the present invention is to provide a master-slave device for a robot to assist medical procedure of an operator by using the force measurement apparatus.

Additional benefits and advantages of the disclosed embodiments will be apparent from the specification and Figures. The benefits and/or advantages may be individually provided by the various embodiments and features of the specification and drawings disclosure, and need not all be provided in order to obtain one or more of the same.

In order to achieve the above objects, the present invention has the following configurations.

In one general aspect, the techniques disclosed here feature: a force measurement apparatus that measures a force generated, in endoscopic surgery in which an operator inserts an instrument into a body of a living body, when the instrument inserted into the body is brought into contact with the living body, the force measurement apparatus comprising:

a force detection unit that is disposed outside the living body and detects a force generated when the instrument having a tip end inserted into the body acts on the living body;

a reference information generating unit that, when the tip end of the instrument is inserted from outside of the living body into the body toward a region to be measured in the body and reaches the region to be measured through a region except for the region to be measured, generates reference information serving as information relating to a force acting on the region except for the region to be measured; and an individual force calculation unit that, when the instrument is inserted into the body of the living body, individually calculates forces generated when the instrument acts on the region to be measured in the body based on information of the force detected by the force detection unit and the reference information generated by the reference information generating unit.

According to the aspects of the present invention, the force measurement apparatus, the force measurement method, the force measurement program, and the force measurement integrated electronic circuit make it possible to measure only the force acting on the tip end of the instrument such as a forceps on the internal body side, from outside the body. Furthermore, by using the force measurement apparatus disposed outside the body, operation assistance can be performed such that only the force acting on the tip end can be fed back to a master machine, and a robot is stopped in a loaded condition.

BRIEF DESCRIPTION OF THE DRAWINGS

These and other aspects and features of the present disclosure will become clear from the following description taken in conjunction with the embodiments thereof with reference to the accompanying drawings, in which:

FIG. 5 is a view showing a table of a reference information database according to the first embodiment of the present invention;

FIG. 6 is a view showing a table of a measurement information database according to the first embodiment of the present invention;

FIG. 15 is a view showing a table of a reference information database according to the second embodiment of the present invention;

DETAILED DESCRIPTION

Figure 1:
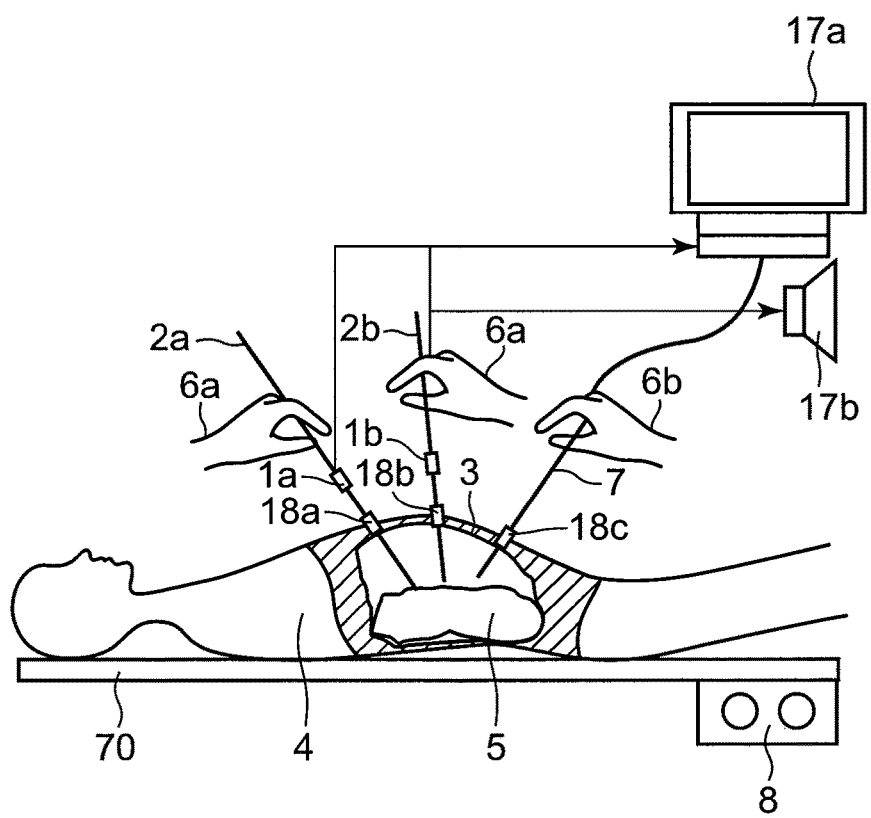
FIG. 1 is a view showing an outline of a configuration of a force measurement apparatus according to a first embodiment of the present invention.

A first embodiment of the present invention will be described below with reference to the drawings.

Various aspects of the present invention will be described before the embodiments of the present invention will be described in detail with reference to the drawings.

Examples of the disclosed technique are as follows.

1st aspect: A force measurement apparatus that measures a force generated, in endoscopic surgery in which an operator inserts an instrument into a body of a living body, when the instrument inserted into the body is brought into contact with the living body, the force measurement apparatus comprising:

a force detection unit that is disposed outside the living body and detects a force generated when the instrument having a tip end inserted into the body acts on the living body;

a reference information generating unit that, when the tip end of the instrument is inserted from outside of the living body into the body toward a region to be measured in the body and reaches the region to be measured through a region except for the region to be measured, generates reference information serving as information relating to a force acting on the region except for the region to be measured; and an individual force calculation unit that, when the instrument is inserted into the body of the living body, individually calculates forces generated when the instrument acts on the region to be measured in the body based on information of the force detected by the force detection unit and the reference information generated by the reference information generating unit.

According to the configuration, the force individually acting on the living body can be calculated based on the force measured from outside the body.

2nd aspect: The force measurement apparatus according to the 1st aspect, wherein the region to be measured is a region to be examined in the body or a region to be treated including a surgery site and a region except for the region to be measured is skin, a body wall, or fat.

3rd aspect: The force measurement apparatus according to the 1st aspect, wherein the reference information generated by the reference information generating unit includes at least two directions intersecting with a direction in which the instrument is inserted into the body of the living body and information of magnitudes of forces in the directions.

With the configuration, the force individually acting on the living body can be calculated based on the forces measured from at least two directions intersecting with each other with reference to the insertion direction of the instrument in the body of the living body.

4th aspect: The force measurement apparatus according to the 3rd aspect, wherein information of the force in the reference information generated by the reference information generating unit is information of displacement of time-series forces.

According to the configuration, the force individually acting on the living body can be calculated based on the time series information relating to the force measured from outside the body.

5th aspect: The force measurement apparatus according to the 1st aspect, further comprising a position orientation acquiring unit that acquires a position or an orientation of the instrument inserted into the body, wherein the reference information of the reference information generating unit is information configured by pairing the position or the orientation of the instrument with the force in a state in which the tip end of the instrument is inserted into the body of the living body and is not in contact with a region in the body, and the individual force calculation unit that, when the tip end of the instrument is inserted into the body of the living body, individually calculates forces generated when the instrument acts on the region in the body based on the information of the force detected by the force detection unit, the position or the orientation of the instrument acquired by the position orientation acquiring unit, and the reference information generated by the reference information generating unit.

According to the configuration, the force individually acting on the living body can be calculated from different directions based on the force measured from outside the body and information relating to the position or the orientation of the instrument.

6th aspect: The force measurement apparatus according to the 5th aspect, further comprising a position orientation acquiring unit that acquires a position or an orientation of the instrument inserted into the body, wherein the reference information of the reference information generating unit is information configured by pairing the position or the orientation of the instrument and the force with time in a state in which the tip end of the instrument is inserted into the body of the living body and is not in contact with a region in the body, the reference information generated by the reference information generating unit includes at least two directions intersecting with a direction in which the instrument is inserted into the body of the living body and information of displacement of time-series forces in the directions, the reference information generating unit that sets, as the reference information, a first time point at which the displacement of the force changes by a predetermined threshold value for setting first time point or more, the individual force calculation unit, when the instrument is inserted into the body of the living body, sets a second time point at which the displacement of the force detected by the force detection unit is a predetermined threshold value for setting second time point or more, sequentially searches a position close to a position of the instrument at the second time point from the first time point, selects the reference information including in a matched position obtained by the searching, and calculates a value obtained by subtracting a force calculated from the selected reference information from the force detected by the force detection unit, as an individual force.

According to the configuration, in calculation of the force individually acting on the living body based on the force measured from outside the body, an operation to acquire the reference information is performed in only at least two directions intersecting with each other with reference to the insertion direction in the body of the living body, making it possible to shorten an operating time.

7th aspect: The force measurement apparatus according to the 1st aspect, further comprising:

a reference information correction notification unit that performs a notice in a case where correction is required after presence/absence of correction of the reference information is detected; and a reference information correction unit that corrects the reference information based on the notice from the reference information correction notification unit.

According to the configuration, the operator can found a timing at which the reference information is to be corrected, correct the reference information, and accurately calculate the force individually acting on the living body based on the force measured from outside the body.

8th aspect: The force measurement apparatus according to the 7th aspect, wherein the reference information correction notification unit, when the individual force calculation unit fails to select the reference information, decides that the reference information need to be corrected and then performs a notice.

According to the configuration, the operator can found a timing at which the reference information is to be corrected, correct the reference information, and accurately calculate the force individually acting on the living body based on the force measured from outside the body.

9th aspect: The force measurement apparatus according to the 1st aspect, comprising a force decision unit, when the force detected by the reference information generating unit or pieces of information of an individual force calculated by the individual force calculation unit is a predetermined threshold value for deciding load or more, decides that a load is applied to a region in the body.

According to the configuration, it can be automatically decided whether the load is applied to the living body.

10th aspect: The force measurement apparatus according to the 7th aspect, comprising a decision result notification unit that displays a force detected by the reference information generating unit, an individual force calculated by the individual force calculation unit, or a decision result decided by the force decision unit such that the force, the individual force, or the decision result is added to an image obtained by capturing the living body.

According to the configuration, the operator can confirm a loading situation together with the image obtained by capturing the living body when the load is applied to the living body.

11th aspect: The force measurement apparatus according to the 7th aspect, comprising a decision result notification unit that notifies the operator of a force detected by the reference information generating unit, an individual force calculated by the individual force calculation unit, or a decision result decided by the force decision unit, through voice.

According to the configuration, the operator can be notified with voice that a load is applied to the living body.

12th aspect: A force measurement method for measuring a force generated, in endoscopic surgery in which an operator inserts an instrument into a body of a living body, when the instrument inserted into the body is brought into contact with the living body, the force measurement method comprising:
causing a force detection unit disposed outside the living body to detect a force generated when the instrument having a tip end inserted into the body of the living body acts on the living body;
causing a reference information generating unit to, when the tip end of the instrument is inserted from outside of the living body into the body toward a region to be measured in the body and reaches the region to be measured through a region except for the region to be measured, generate reference information serving as information relating to a force acting on the region except for the region to be measured; and
causing an individual force calculation unit to, when the instrument is inserted into the body of the living body, individually calculate forces generated when the instrument acts on the region to be measured in the body based on information of the force detected by the force detection unit and the reference information generated by the reference information generating unit.

According to the configuration, the force individually acting on the living body can be calculated based on the force measured from outside the body.

13th aspect: A force measurement program for measuring a force generated, in endoscopic surgery in which an operator inserts an instrument into a body of a living body, when the instrument inserted into the body is brought into contact with the living body, the force measurement program causing a computer to execute steps of:
causing a force detection unit disposed outside the living body to detect a force generated when the instrument having a tip end inserted into the body of the living body acts on the living body;
causing a reference information generating unit to, when the tip end of the instrument is inserted from outside of the living body into the body toward a region to be measured in the body and reaches the region to be measured through a region except for the region to be measured, generate reference information serving as information relating to a force acting on the region except for the region to be measured; and
causing an individual force calculation unit to, when the instrument is inserted into the body of the living body, individually calculate forces generated when the instrument acts on the region to be measured in the body based on information of the force detected by the force detection unit and the reference information generated by the reference information generating unit.

According to the configuration, the force individually acting on the living body can be calculated based on the force measured from outside the body.

14th aspect: A force measurement integrated electronic circuit that measures a force generated, in endoscopic surgery in which an operator inserts an instrument into a body of a living body, when the instrument inserted into the body is brought into contact with the living body, the force measurement integrated electronic circuit comprising:
a force detection unit that is disposed outside the living body and detects a force generated when the instrument having a tip end inserted into the body of the living body acts on the living body;
a reference information generating unit that, when the tip end of the instrument is inserted from outside of the living body into the body toward a region to be measured in the body and reaches the region to be measured through a region except for the region to be measured, generates reference information serving as information relating to a force acting on a region except for the region to be measured; and
an individual force calculation unit that, when the instrument is inserted into the body of the living body, individually calculates forces generated when the instrument acts on the region to be measured in the body based on information of the force detected by the force detection unit and the reference information generated by the reference information generating unit.

According to the configuration, the force individually acting on the living body can be calculated based on the force measured from outside the body.

15th aspect: A master-slave device that includes a slave mechanism that inserts an instrument into a body of a living body in endoscopic surgery and a master mechanism that is operated by an operator so as to remote-control the slave mechanism, the master-slave device comprising a force measurement apparatus disposed in the instrument outside the body,
the force measurement apparatus comprising:
a force detection unit that is disposed outside the living body and detects a force generated when the instrument having a tip end inserted into the body of the living body acts on the living body;
a reference information generating unit that, when the tip end of the instrument is inserted from outside of the living body into the body toward a region to be measured in the body and reaches the region to be measured through a region except for the region to be measured, generates reference information serving as information relating to a force acting on a region except for the region to be measured; and
an individual force calculation unit that, when the instrument is inserted into the body of the living body, individually calculates forces generated when the instrument acts on the region to be measured in the body based on information of the force detected by the force detection unit and the reference information generated by the reference information generating unit,
the master-slave device further comprising:
a force transmitting portion determination unit that determines a force transmitted from the slave mechanism to the master mechanism based on information of the force calculated by the force measurement apparatus;

a force correction unit that corrects the force when the force is switched to the force determined by the force transmitting portion determination unit;

a force transmitting unit that transmits information of the force corrected by the force correction unit to the master mechanism;

a master control unit that, when the operator operates the master mechanism based on the information of the force of the force transmitting unit, converts operation information of the master mechanism into an electric signal; and a slave control unit that is connected to the slave mechanism and the master control unit and outputs a control signal that transmits the operation information of the master mechanism transmitted from the master control unit to the slave mechanism, wherein based on the control signal transmitted from the slave control unit, the slave mechanism is operated to perform a slave operation.

16th aspect: The master-slave device according to the 15th aspect, wherein the force measurement apparatus includes a force decision unit that decides that a load is applied to the living body when information of an individual force calculated by the individual force calculating unit is a predetermined threshold value for deciding load or more, the master-slave device further includes a slave operation generating unit that generates an operation to stop a slave operation by the slave mechanism when the force decision unit decides that the force information is the predetermined threshold for deciding load or more and that a load is applied to the living body, and the slave control unit controls the slave mechanism based on the operation generated by the slave operation generating unit.

First Embodiment

An outline of a force measurement apparatus 1 according to a first embodiment of the present invention will be described.

The force measurement apparatus 1 measures, in endoscopic surgery performed such that an operator 6a inserts an instrument into a body of a living body 4, a force acting when the instrument inserted into the body is brought into contact with the living body 4.

The force measurement apparatus 1 includes at least a force detection unit 13, a reference information generating unit 15, and an individual force calculation unit 11. In the first embodiment, the force measurement apparatus 1 further includes a measurement information generating unit 44.

The force detection unit 13 is disposed outside the living body 4 and detects a force generated when an instrument with a tip end being inserted into the body of the living body 4 acts on the living body 4.

The reference information generating unit 15 generates reference information serving as information relating to a force generated in a state in which the tip end of the instrument is inserted into the body of the living, body 4 and is not brought into contact with an in-body portion (region to be measured, for example, a surgery site) 5.

When the instrument is inserted into the body of the living body 4, the individual force calculation unit individually calculates forces generated when the instrument acts on internal body regions (for example, two portions including an abdominal wall 3 serving as an example of a region except for the region to be measured and an internal organ 5 serving as an example of the region to be measured) based on information of the force detected by the force detection unit 13 and the reference information generated by the reference information generating unit 15. In the first embodiment, the individual force calculation unit 11 includes a reference information selecting unit 16 and a calculation unit 11a for individual force calculation.

The force measurement apparatus 1 will be described below in detail.

FIG. 1 shows a manner of endoscopic surgery serving as an example using the force measurement apparatus 1.

Trocars 18a, 18b, and 18c are inserted into a plurality of (for example, three) holes formed in the abdomen of a human body 4 on a bed 70, respectively, and a forceps 2a, a forceps 2b, and an endoscope 7 are inserted into the holes of the trocars 18a, 18b, and 18c, respectively.

A video image (still image) of the endoscope 7 is displayed on a monitor 17a, and the operator 6a operates the forceps 2a and the forceps 2b serving as an example of instruments while checking the video image. The following description, with respect to the forceps 2a and the forceps 2b, will be made by using the forceps 2a as a typical example. An operator 6b operates the endoscope 7.

In this example, as the force measurement apparatus 1, a force measurement apparatus 1a is used for the forceps 2a, and a force measurement apparatus 1b is used for the forceps 2b. Each of the force measurement apparatus 1a and the force measurement apparatus 1b has the same configuration as that of force measurement apparatus 1.

The force measurement apparatus 1a and the force measurement apparatus 1b are respectively fixed between grip portions of the forceps 2a and the forceps 2b for the operator 6a and the abdominal wall 3 of the living body 4 and are disposed at positions that do not enter the body before and after the forceps 2a and the forceps 2b are inserted into the body. In other words, the force measurement apparatus 1a and the force measurement apparatus 1b are always disposed outside the body. Forces generated when the operator 6a operates the forceps 2a and the forceps 2b to insert the forceps 2a and the forceps 2b into the trocar 18a and the trocar 18b, respectively and forces generated when the end tips of the forceps 2a and the forceps 2b are brought into contact with the internal organ 5, respectively are individually measured by the force measurement apparatus 1a and the force measurement apparatus 1b to display measurement results on the monitor 17a. Furthermore, when the force measurement apparatus 1a and the force measurement apparatus 1b measure forces such that a load is applied to the internal organ 5 or the abdominal wall 3 of the living body 4, the monitor 17a and a loudspeaker 17b notify the operator of a warning.

The operator 6a performs surgery while checking a video image displayed on the monitor 17a, a value measured by the force measurement apparatuses 1a, 1b, or the presence/absence of a warning.

An input IF 8 is an operational interface that is disposed in, for example, a lower portion of the bed 70 and gives instructions for starting or ending measurements of the force measurement apparatuses 1a, 1b, and is configured by, for example, a button or the like.

Figure 2:
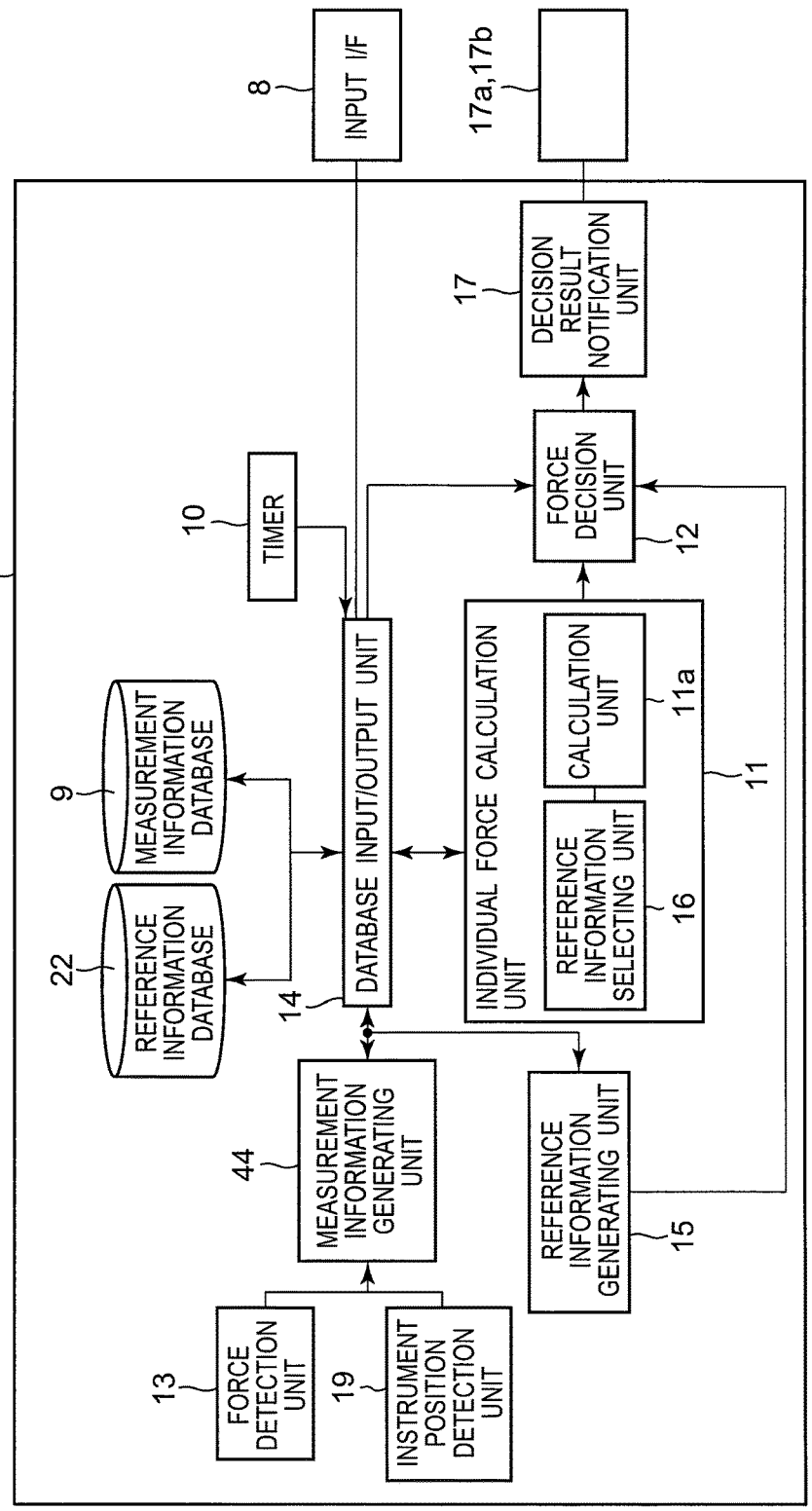
FIG. 2 is a block diagram showing a detailed configuration of the force measurement apparatus according to the first embodiment of the present invention.

FIG. 2 shows a configuration of the force measurement apparatus 1(1a, 1b).

In addition to the force detection unit 13, the reference information generating unit 15, and the individual force calculation unit 11 as described above, the force measurement apparatus 1 according to the first embodiment includes a database input/output unit 14, a measurement information database 9, a reference information database 22, a timer 10, an instrument position detection unit 19 functioning as an example of a position orientation acquiring unit, a force decision unit 12, and a decision result notification unit 17. The configurations of the units will be described below in detail.

<<Force Detection Unit 13>>

The force detection unit 13 detects a force generated when the forceps 2a or the forceps 2b is brought into contact with the trocar 18a or 18b or the human body 4, from outside the human body 4, and outputs the detection result to the database input/output unit 14 and the reference information generating unit 15. For example, as an example of the force detection unit 13, a one-axis force sensor that measures a force in a one-axis direction, i.e., an insertion direction is employed, and, as shown in FIG. 1, is disposed on an external body portion of the forceps 2a, 2b. The operator 6a operates the forceps 2a or the forceps 2b and measures a sum of a force T1 acting on the abdominal wall 3 as a load when the forceps 2a or 2b passes through the trocar 18a or 18b and a force T2 generated when the tip end of the forceps 2a or 2b acts on the internal organ 5.

Figure 3:
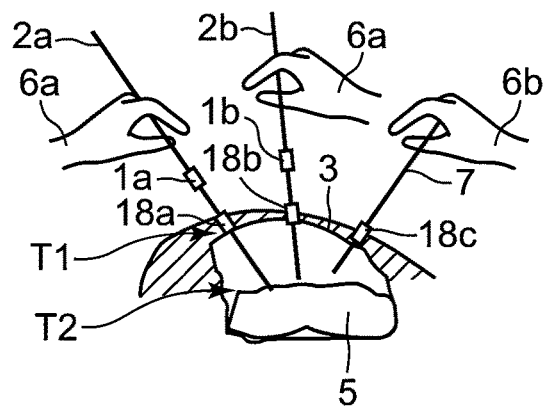
FIG. 3 is a view for describing an operation of endoscopic surgery in the first embodiment of the present invention.

For example, when the forces T1 and T2 are generated at the portions of the human body 4 as shown in FIG. 3, since the force detection unit 13 cannot individually detect the forces T1 and T2, the force detection unit 13 measures a sum T (in this example, T=T1+T2) of the forces. The values of the forces detected by the force detection unit 13 are detected by the force detection unit 13 every predetermined period of time (for example, every 4 msec) through the use of the timer 10 (will be described later), are output with time from the force detection unit 13 to the database input/output unit (will be described later), and are stored in the measurement information database 9 or the reference information database 22.

As the force detection unit 13 according to the first embodiment, as an example, a one-axis force sensor that detects only a force in a one-axis direction is used. However, alternatively, as another example of the force detection unit 13, a force sensor that can measure forces in 3-axis directions, i.e., x, y, and z axes, or a 6-axis force sensor that can measure the forces in the 3-axis directions and torques around the 3-axis directions may be used.

<<Timer 10>>

The timer 10 is connected to the database input/output unit 14 to execute the database input/output unit 14 after a predetermined period of time (for example, every 4 msec) has elapsed.

<<Database Input/Output Unit 14>>

The database input/output unit 14 performs data input/output operations among the measurement information database 9, the reference information database 22, the force detection unit 13, the instrument position detection unit 19, the reference information generating unit 15, the individual force calculation unit 11, and the force decision unit 12.

<<Instrument Position Detection Unit 19>>

Figure 4:
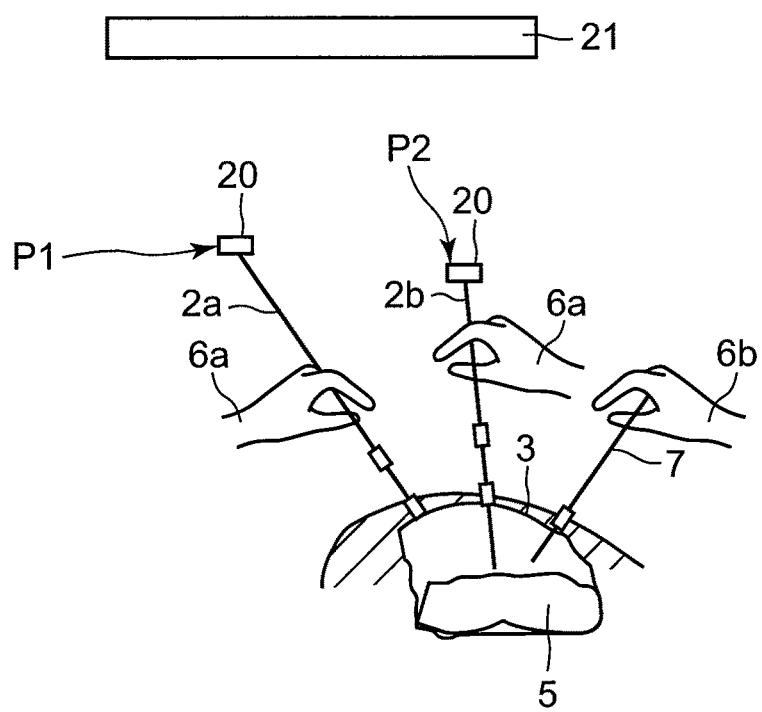
FIG. 4 is a view for describing an example of an instrument position detection unit according to the first embodiment of the present invention.

The instrument position detection unit 19 functions as an example of a position orientation acquiring unit that acquires positions or orientations of the forceps 2a and the forceps 2b inserted into the body. More specifically, the instrument position detection unit 19 detects tip-end positions (positions P1 and P2 in FIG. 4) of the forceps 2a and the forceps 2b on an opposite side of the internal organ 5, and outputs the detection result to the database input/output unit 14 and the reference information generating unit 15. For example, the instrument position detection unit 19 is configured by a 3-axis magnetic type position measurement sensor shown in FIG. 4, magnetic force measurement units 20 are attached to the tip-end positions (positions P1 and P2 in FIG. 4) of the forceps 2a and 2b on the opposite position of the internal organ 5, and a magnetic field is generated by a magnetic field source 21 to cause the instrument position detection unit 19 to detect the positions P1 and P2 of the forceps 2a and 2b. Information of the positions detected by the instrument position detection unit 19 is output from the instrument position detection unit 19 to the database input/output unit 14 (will be described later) together with time through the use of the timer 10 every predetermined period of time (for example, every 4 msec), and is stored in the measurement information database 9 or the reference information database 22.

As an example, the instrument position detection unit 19 according to the first embodiment is of a magnetic type. However, as another example of the instrument position detection unit 19, a system in which markers are disposed at the tip-end positions (positions P1 and P2 in FIG. 4) of the forceps 2a and the forceps 2b on the opposite side of the internal organ 5 and the marker positions of the tip ends of the forceps are detected by using a camera, or a system in which the tip ends of the forceps are detected by an infrared sensor may be used. Although the tip-end positions of the forceps 2a and 2b are detected in coordinates of 3-axis directions, when the forceps 2a and the forceps 2b move in a direction orthogonal to the insertion direction with reference to the trocar 18a at a part of the abdominal wall 3, in order to specify the positions of the forceps 2a and 2b, coordinates (coordinates of 3-axis directions and coordinates of rotational angles around the respective axes) of 6-axis directions in which the positions and the orientations of the forceps 2a and 2b can be measured may be detected.

<<Reference Information Generating Unit 15>>

The reference information generating unit 15, based on pieces of information from the instrument position detection unit 19, the force detection unit 13, and the database input/output unit 14, generates reference information and outputs the reference information to the database input/output unit 14 and the force decision unit 12. The reference information is information relating to a force acquired when the operator 6 moves the forceps 2a, 2b in a predetermined direction in a state in which the tip ends of the forceps 2a, 2b pass through the abdominal wall 3, are inserted into the body of the living body 4, and are not in contact with the surgery site 5. The reference information is used when a force generated when the forceps 2a, 2b acts inside the body is individually calculated from outside the body (individual force is calculated). More specifically, the reference information is information configured by pairing the positions (moving direction of the forceps 2a) or the orientations of the forceps 2a, 2b detected by the instrument position detection unit 19 before the forceps 2a, 2b pass through the abdominal wall 3, are inserted into the body, and are brought into contact with the internal organ 5, a value of a force detected by the force detection unit 13, and a reference information reference point calculated by a method (will be described later) with time. The force information included in the reference information is also called displacement information of time-series forces. The reference information reference point is set to a time point at which a displacement of a force detected by the force detection unit 13 changes by a predetermined first threshold value (threshold value for setting reference point or threshold value for setting first time point) (for example, 0.1 N) or more. The "reference information reference point" mentioned here means a time point serving as a reference to individually measure (calculate) forces that respectively act based on the sum of forces detected by the force detection unit 13. The reference information generating unit 15 sets a start point of reference information generation as the first reference point.

The generation of the reference information by the reference information generating unit 15 is started by reference information generation start instructions generated from the input IF 8 through the database input/output unit 14, and the reference information generating unit 15 generates the pieces of reference information every predetermined period of time (for example, every 4 msec) through the use of the timer 10.

The reference information generated by the reference information generating unit 15 is output to the database input/output unit 14 together with time and stored in the reference information database 22. A detailed method of generating reference information will be described later.

—Reference Information Database 22—

The reference information database 22 stores the reference information generated by the reference information generating unit 15 through the database input/output unit 14 together with time through the use of the timer 10. As needed, the reference information is read out from the reference information database 22 by the database input/output unit 14. The reference information, as described above, is information configured by pairing information relating to a force detected by the force detection unit 13, positions of the forceps 2a, 2b detected by the instrument position detection unit 19 before the forceps 2a, 2b are brought into contact with the internal organ 5, and a reference point calculated by the reference information generating unit 15 with time. More specifically, out of the reference information, the information relating to the force detected by the force detection unit 13, the positions of the forceps 2a, 2b detected by the instrument position detection unit 19 before the forceps 2a, 2b are brought into contact with the internal organ 5, and the reference point calculated by the reference information generating unit 15 are generated by the reference information generating unit 15 every predetermined period of time (for example, every 4 msec) through the use of the timer 10, are output from the reference information generating unit 15 to the database input/output unit 14 together with time, and are stored in the reference information database 22 as the reference information.

FIG. 5 shows an example of the contents of the reference information of the reference information database 22.

(1) A column for "time" shows information relating to time at which the forceps 2a and 2b are inserted. In the first embodiment, the time is shown in units of milliseconds (msec).

(2) A column for "force" shows information of a force detected by the force detection unit 13. In the first embodiment, a force in an insertion direction is shown in units of newton (N), and a force in a rotational direction is shown in units of newton meter (Nm).

(3) A column for "position" shows respective positions of the forceps 2a and 2b detected by the instrument position detection unit 19. In the first embodiment, a position is shown in units of meter (m).

(4) A column for "reference point" shows a reference point set by the reference information generating unit 15. "1" is set in the corresponding time column when the reference point is set, "0" is set in the corresponding time column when the reference point is not set, and "0" is set as a default value.

(5) A column for "ID" shows a sign used to identify reference information. More specifically, the same ID is set in a period of time from a reference point set by the reference information generating unit 15 to the next reference point.

<<Measurement Information Generating Unit 44>>

The measurement information generating unit 44 generates the measurement information database 9 based on the pieces of information from the instrument position detection unit 19, the force detection unit 13, and the database input/output unit 14, and outputs information of the measurement information database 9 to the database input/output unit 14. Measurement information includes information relating to the force detected by the force detection unit 13, positions of the forceps 2a and 2b detected by the instrument position detection unit 19 before and after the forceps 2a and 2b are brought into contact with the internal organ 5, and information of a force calculated by the calculation unit 11a of the individual force calculation unit 11 (will be described later).

—Measurement Information Database 9—

The information relating to the force detected by the force detection unit 13 and the positions of the forceps 2a and 2b detected by the instrument position detection unit 19 before and after the forceps 2a and 2b are brought into contact with the internal organ 5 are generated by the measurement information generating unit 44 through the database input/output unit 14 every predetermined period of time (for example, every 4 msec) through the use of the timer 10, are output from the measurement information generating unit 44 to the database input/output unit 14 with time, and are stored in the measurement information database 9 as measurement information. Furthermore, in the measurement information database 9, these pieces of information described above, the ID of the reference information selected by the reference information selecting unit 16 of the individual force calculation unit 11, the individual force calculated by the calculation unit 11a of the individual force calculation unit 11 are paired with time and stored. As needed, the measurement information from the measurement information database 9 is read out from the database input/output unit 14.

FIG. 6 shows an example of the contents of the measurement information in the measurement information database 9.

(1) A column for "time" shows information relating to time at which the forceps 2a and 2b are inserted. In the first embodiment, the time is shown in units of milliseconds (msec).

(2) A column for "force" shows information of a force detected by the force detection unit 13. In the first embodiment, a force in an insertion direction is shown in units of newton (N), and a force in a rotational direction is shown in units of newton meter (Nm).

(3) A column for "position" shows positions and orientations of the forceps 2a and 2b detected by the instrument position detection unit 19. In the first embodiment, a position is shown in units of meter (m).

(4) A column for "ID of reference information" shows an ID of reference information selected by the reference information selecting unit 16 of the individual force calculation unit 11.

(5) A column for "individual force" shows information of a force calculated by the calculation unit 11a of the individual force calculation unit 11. In the first embodiment, a force in an insertion direction is shown in units of newton (N), and a force in a rotational direction is shown in units of newton meter (Nm).

<<Individual Force Calculation Unit 11>>

The individual force calculation unit 11, when the forceps 2a, 2b are inserted into the body of a living body, sets an individual force calculation reference point at which a displacement of the force detected by the force detection unit 13 is a third threshold value (threshold value for setting individual force calculation reference point) or more, sequentially searches positions close to the positions of the forceps 2a, 2b at the individual force calculation reference point from the reference points of the reference information, causes the reference information selecting unit 16 to select reference information including the matched position obtained by the searching, and causes the calculation unit 11a to calculate, as an individual force, a value obtained by subtracting a force calculated based on the selected reference information from the force detected by the force detection unit 13. More specifically, in the calculation unit 11a of the individual force calculation unit 11, based on the reference information stored in the reference information database 22 through the database input/output unit 14, individual forces generated when the forceps 2a and 2b are brought into contact with the internal organ 5 are calculated based on the reference information and the force(s) detected by the force detection unit 13. The reference information used in the reference information selecting unit 16 of the individual force calculation unit 11 is selected by the reference information selecting unit 16 based on the present (force measurement-time) positions of the forceps 2a and 2b from the reference information read out from the reference information database 22 by the database input/output unit 14. The reference information selecting unit 16 selects reference information closest to the present (force measurement-time) positions (however, positions of axes orthogonal to insertion directions except for positions in the insertion directions) of the forceps 2a and 2b from positions of the forceps 2a and 2b before the forceps 2a and 2b pass through the abdominal wall 3 and the tip ends thereof are brought into contact with the internal organ 5. The ID of the reference information selected by the reference information selecting unit 16 is stored from the reference information selecting unit 16 as an "ID of reference information" of the measurement information database 9 through the database input/output unit 14.

The individual force calculation unit 11 detects individual forces acting when the forceps 2a and 2b are brought into contact with the internal organ 5 based on the reference information selected by the reference information selecting unit 16. More specifically, based on the reference information read out from the reference information database 22 by the database input/output unit 14, the reference information selecting unit 16 selects reference information at a time point at which the reference information is desired to be measured. Next, a value obtained by subtracting a value of a force of the reference information selected by the reference information selecting unit 16 from the value of the force measurement unit 13 at that time point is calculated by the calculation unit 11a of the individual force calculation unit 11, as an individual force. The individual force calculated by the calculation unit 11a of the individual force calculation unit 11 is stored from the calculation unit 11a of the individual force calculation unit 11 into the measurement information database 9 through the database input/output unit 14. A detailed calculating method performed by the calculation unit 11a of the individual force calculation unit 11 will be described later.

<<Force decision unit 12>>

The force decision unit 12, based on the pieces of information obtained from the database input/output unit 14, the individual force calculation unit 11, and the reference information generating unit 15, decides whether a load is applied to the abdominal wall 3 based on a force generated by the reference information generating unit 15. More specifically, when the force decision unit 12 decides that the force generated by the reference information generating unit 15 is a predetermined second threshold value (threshold value for deciding an abdominal wall load) (for example, 2 N) or more, the force decision unit 12 decides that a load is applied to the abdominal wall 3 based on the force generated by the reference information generating unit 15. Furthermore, when the force decision unit 12 decides that the force calculated by the calculation unit 11a of the individual force calculation unit 11 is a predetermined fourth threshold value (threshold value for deciding an internal organ load) (for example, 2 N) or more, the force decision unit 12 decides that a load is applied to the internal organ 5 based on the force calculated by the calculation unit 11a of the individual force calculation unit 11. A decision result is output from the force decision unit 12 to the decision result notification unit 17 together with the force used in the decision.

<<Decision Result Notification Unit 17>>

Figure 7A:
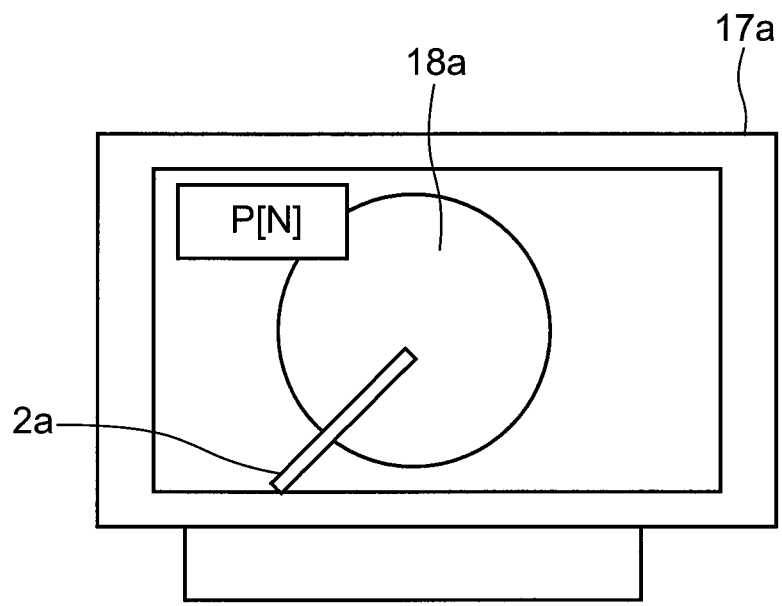
FIG. 7A is a view of a monitor for describing an example of a notice obtained by a decision result notification unit according to the first embodiment of the present invention.
Figure 7B:
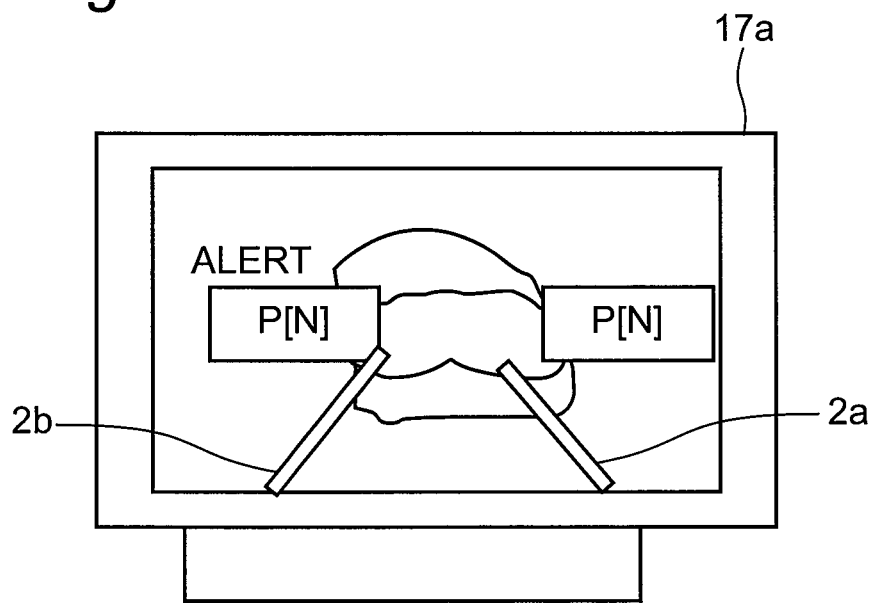
FIG. 7B is a view of the monitor for describing an example of the notice obtained by the decision result notification unit according to the first embodiment of the present invention.

The decision result notification unit 17, based on the information from the force decision unit 12, notifies the operator 6 of a decision result obtained by the force decision unit 12 through a decision result notification device or the like. As the decision result notification device that notifies the operator 6 through the decision result notification unit 17, for example, the monitor 17a, the loudspeaker 17b, or the like can be employed. More specifically, as shown on the monitor 17a in FIG. 7A, when a force acting when the forceps 2a is brought into contact with the trocar 18a is calculated by the reference information generating unit 15 and decides by the force decision unit 12, near a position where the forceps 2a and the trocar 18a are displayed, a force calculated by the reference information generating unit 15 or an individual force P [N] calculated by the calculation unit 11a of the individual force calculation unit 11 is displayed together with a video image (still image) of an endoscope. At this time, when the force decision unit 12 decides that a load is applied to the abdominal wall 3 from the forceps 2a through the trocar 18a, like "ALERT" or the like, a warning (example of a decision result obtained by the force decision unit 12) is displayed by the decision result notification unit 17. More specifically, FIG. 7A shows a view obtained when reference information is generated without the forceps 2a being brought into contact with the internal organ 5. On the other hand, as shown in FIG. 7B, when a force acting when the forceps 2a further moves toward the internal organ 5 and is brought into contact with the internal organ 5 is calculated by the calculation unit 11a of the individual force calculation unit 11, an individual force P [N] calculated by the calculation unit 11a of the individual force calculation unit 11 is displayed together with a video image (still image) of an endoscope. At this time, when the force decision unit 12 decides that the forceps 2a places a load on internal organ 5, like "ALERT" or the like, a warning (example of a decision result obtained by the force decision unit 12) is displayed by the decision result notification unit 17, and an individual force obtained at this time is displayed by the decision result notification unit 17. When the force decision unit 12 decides that there is a load applied by the forceps 2a, in place of the image display, or in addition to the image display, a warning sound may be made by the loudspeaker 17b, and a warning may be given to the operator 6 by the decision result notification unit 17.

Figure 8:
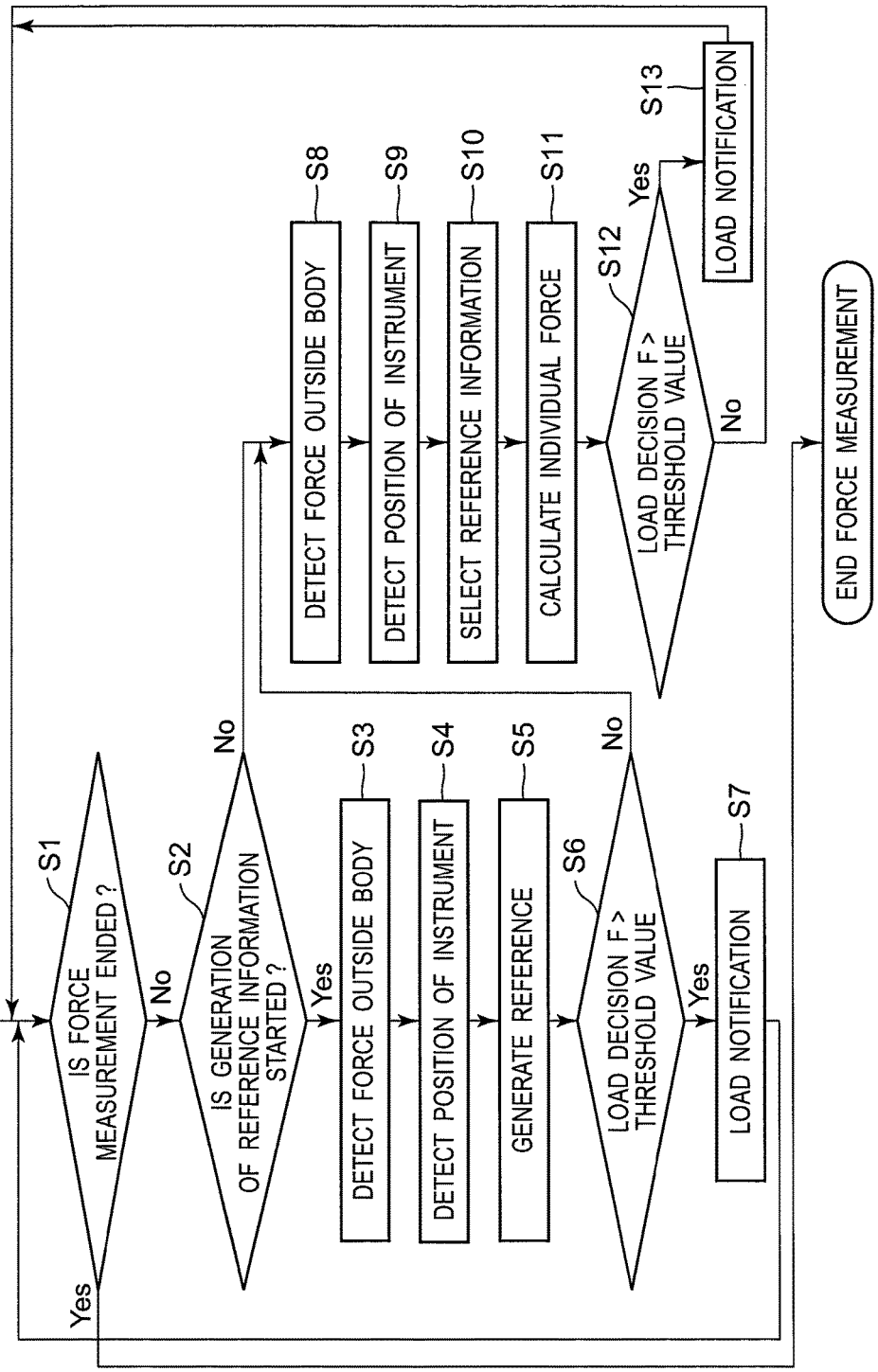
FIG. 8 is a flow chart of a force measurement process of the force measurement apparatus according to the first embodiment of the present invention.

Operational steps of a force measurement process in the force measurement apparatus 1 according to the first embodiment will be described below. FIG. 8 is a flow chart of the force measurement process of the force measurement apparatus 1 according to the first embodiment. In this case, as shown in FIGS. 9A to 9D, a task in which the forceps 2a is inserted from a hole formed in the abdominal wall 3 into a human body 4 through the trocar 18a in a downward direction from above the human body 4 will be exemplified. A state in FIG. 9B or FIG. 9C is a state in which the forceps 2a is not brought into contact with the internal organ 5 and reference information is generated. FIG. 9D shows a state in which the forceps 2a is brought into contact with the internal organ 5. Thus, the following reference information generating operation is performed in states in FIGS. 9A to 9C.

First, when receiving start instructions for force measurement via the input IF 8, the force measurement apparatus 1 starts force measurement.

In step S1, when receiving end instructions for force measurement via the input IF 8, the force measurement apparatus 1 ends the force measurement. When the end instructions for force measurement are not input, the force measurement process proceeds to next step S2.

Next, in step S2, when generation start instructions for reference information are input via the input IF 8, the force measurement process proceeds to step S3. When the generation start instructions for reference information are not input, the force measurement process proceeds to step S8. For example, when the process proceeds to steps S3 and S4 and reference information is generated in step S5 once in one surgical operation, in the next and subsequent surgical operations, there are no reference information generation start instructions in step S2, and the reference information that has been already generated can be used without generating reference information.

Figure 9A:
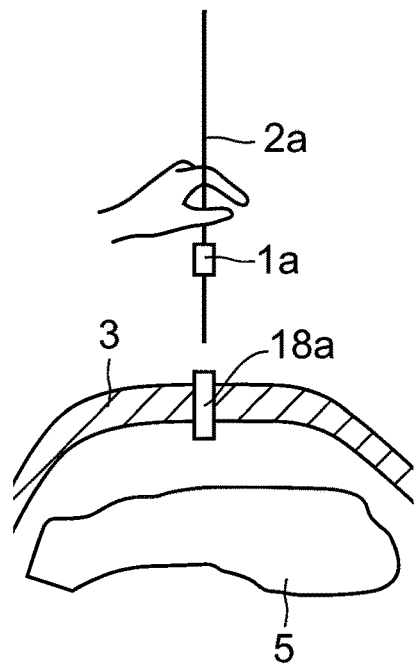
FIG. 9A is a view for describing an operation of endoscopic surgery in the first embodiment of the present invention.
Figure 9B:
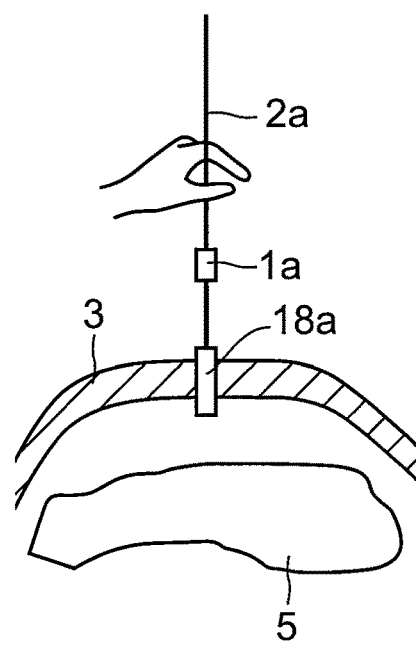
FIG. 9B is a view for describing the operation of the endoscopic surgery in the first embodiment of the present invention.
Figure 9C:
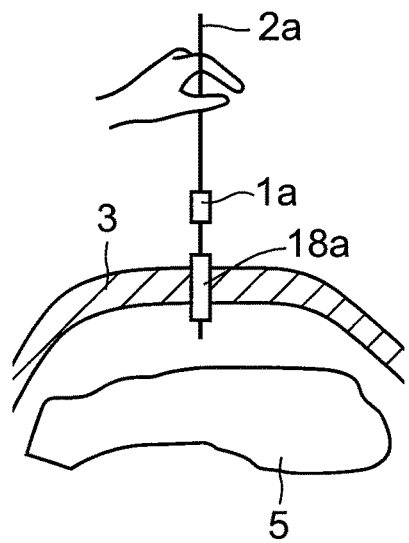
FIG. 9C is a view for describing the operation of the endoscopic surgery in the first embodiment of the present invention.
Figure 9D:
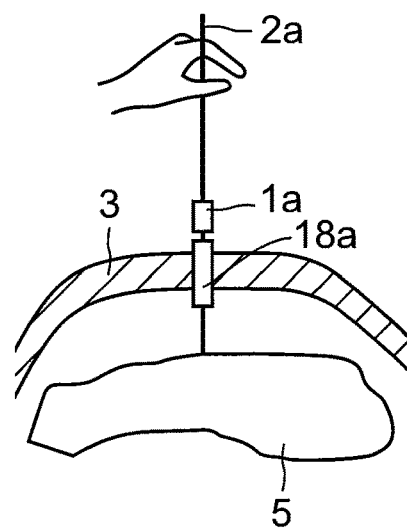
FIG. 9D is a view for describing the operation of the endoscopic surgery in the first embodiment of the present invention.

Next, in step S3, in a state in which the forceps 2a is inserted into the body and is not brought into contact with the internal organ 5 in FIG. 9A to 9B or 9C, the force detection unit 13 detects a force acting on the forceps 2a serving as an example of an instrument from outside the body (see FIGS. 9B and 9C).

Next, in step S4, in a state in which the forceps 2a is not brought into contact with the internal organ 5, the instrument position detection unit 19 detects a position of the forceps 2a from outside the body (see FIGS. 9B and 9C).

Figure 10A:
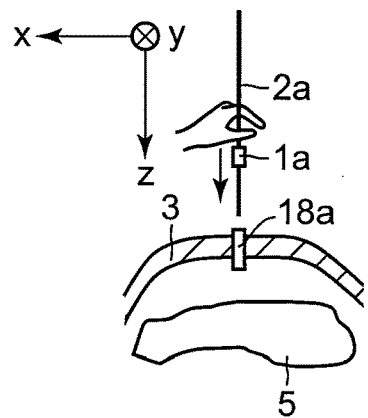
FIG. 10A is a view for describing the operation of the endoscopic surgery in the first embodiment of the present invention.
Figure 10B:
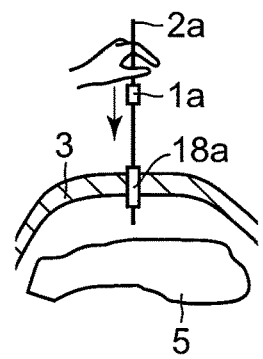
FIG. 10B is a view for describing the operation of the endoscopic surgery in the first embodiment of the present invention.
Figure 10C:
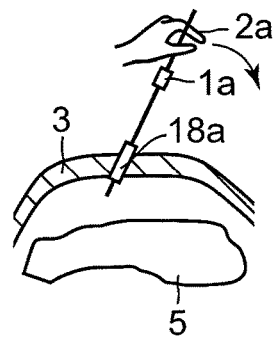
FIG. 10C is a view for describing the operation of the endoscopic surgery in the first embodiment of the present invention.
Figure 10D:
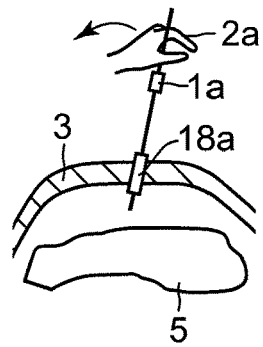
FIG. 10D is a view for describing the operation of the endoscopic surgery in the first embodiment of the present invention.
Figure 10E:
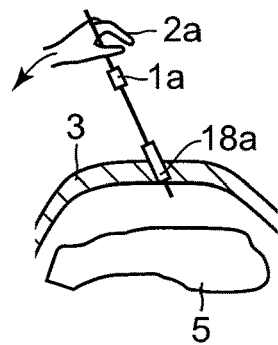
FIG. 10E is a view for describing the operation of the endoscopic surgery in the first embodiment of the present invention.
Figure 10F:
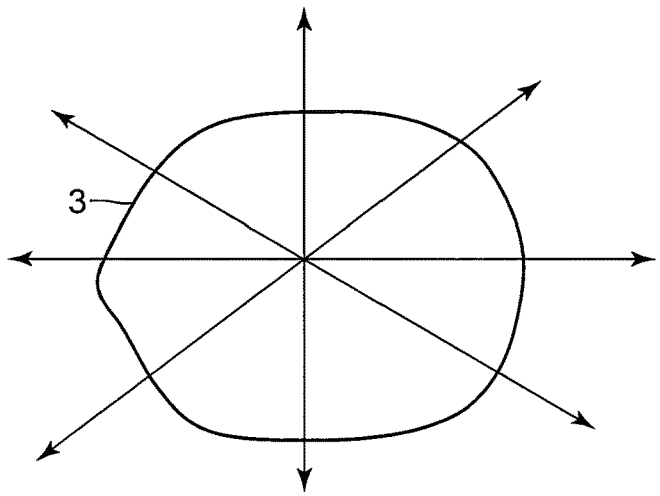
FIG. 10F is a view for describing the operation of the endoscopic surgery in the first embodiment of the present invention.

Next, in step S5, the reference information generating unit 15 generates reference information by calculating a reference point based on the force detected in step S3 and the position of the forceps 2a detected in step S4. More specifically, as shown in FIGS. 10B to 10E of FIGS. 10A to 10E, information of a position and a force of the forceps 2a in a state in which the forceps 2a is caused to pass through the abdominal wall 3 from outside the body and has a tip end on the inner side of the body that is not brought into contact with the internal organ 5 is acquired by the reference information generating unit 15. More specifically, the forceps 2a is inclined from a central position (see FIG. 10B) in one direction to acquire reference information (see FIGS. 10B and 10C). Thereafter, after the forceps 2a is returned to the central position (see FIG. 10D) again, the forceps 2a is moved to be inclined in the next other direction to acquire another piece of reference information (see FIGS. 10D to 10E). In this manner, pieces of reference information are acquired with respect to predetermined directions. Next, reference points are calculated based on the information of the forces in the reference information generating unit 15. Next, reference information obtained by pairing the position and the force of the forceps 2a with the reference point is generated by the reference information generating unit 15. FIG. 10F is a view showing the structures in FIGS. 10A to 10E when viewing from above. As shown in FIG. 10F, in a state in which the tip end of the forceps 2a passes through the abdominal wall 3, is inserted into the body of the living body 4, and is not brought into contact with the surgery site 5, the operator 6 moves the forceps 2a from the center in predetermined directions to cause the reference information generating unit 15 to generate reference information. In this case, the predetermined direction is, for example, 8 directions (upper and lower, left and right, obliquely upper right, obliquely upper left, obliquely lower right, and obliquely lower left directions) including 4 directions orthogonal to each other. The forceps 2a is moved such that the forceps 2a is inclined from the central position in one direction, returned to the central position again, and then included in the next other direction. When the reference information is generated, a direction in which the forceps 2a is moved from the central position is not limited to the 8 directions. At least the forceps 2a must be moved in at least two directions (for example, a muscle fiber direction and a direction orthogonal to the muscle fiber direction; or a longitudinal direction of the trocar 8a, a direction in which the forceps 2a comes close to a surgery site with reference to the central position of the forceps 2a located to have a longitudinal direction parallel to the longitudinal direction of the trocar 8a, and a direction orthogonal to the direction in which the forceps 2a comes close to the surgery site) intersecting with a direction in which the forceps 2a is inserted into the body. At this time, the forceps 2a is kept from coming in contact with an internal organ at all. At a time point in FIG. 10A, since the forceps 2a has not passed through the abdominal wall 3 yet, the reference information has not been generated by the reference information generating unit 15. For this reason, when the forceps 2a reaches a position shown in FIG. 10B, the operator 6 gives instructions for starting generation of reference information through the input IF 8.

Figure 11:
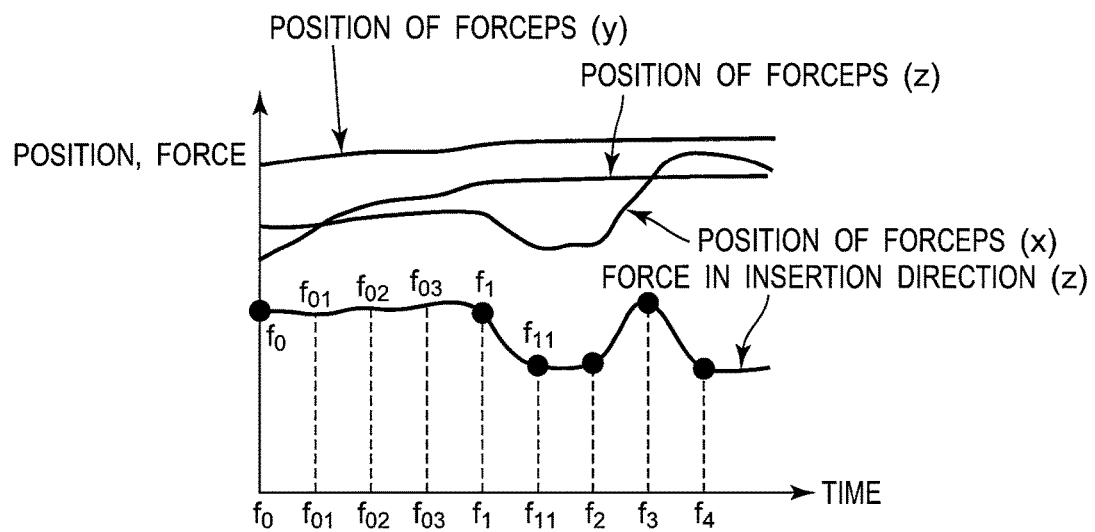
FIG. 11 is a graph showing a relationship between a force in an insertion state and a position of an instrument and time in the first embodiment of the present invention.

FIG. 11 is a graph showing, as in FIGS. 10B to 10E, a relationship between time and the positions and the forces of the forceps 2a from a time point when generation of the reference information is started via the input IF 8. The insertion direction of the forceps 2a is defined as a z axis, and directions orthogonal to the insertion direction are defined as an x axis and a y axis, respectively.

A time point when generation of the reference information is started (time point $t_0$ in FIG. 11) is set as the first reference point by the reference information generating unit 15. Next, in a state in which the tip end of the forceps 2a passes through the abdominal wall 3, is inserted into the body of the living body 4, and is not in contact with the surgery site 5, the operator 6 causes the reference information generating unit 15 to compare absolute values of displacements of forces detected by the force detection unit 13 each time a predetermined period of time has passed while moving the forceps 2a in the predetermined direction, and sets a time point at which the difference changes by a predetermined first threshold value (for example, 0.1 N) or more, as a reference point in the reference information generating unit 15. More specifically, a force obtained at a reference point $t_0$ in FIG. 11 is represented by $f_0$, a force obtained at a time point $t_{01}$ is defined as $f_{01}$, and a force obtained at a time point $t_{02}$ is defined as $f_{02}$. In this case, $\Delta f_{01} = |f_{01} - f_0|$ and $\Delta f_{02} = |f_{02} - f_{01}|$ are compared with each other by the reference information generating unit 15. Next, the reference information generating unit 15 calculates the difference to check whether the difference is the predetermined first threshold value or more. In this example, since the difference is the predetermined threshold first value or less, the reference information generating unit 15 does not set the time point $t_{01}$ as a reference point. Next, the reference information generating unit 15 sequentially compares transitions of forces obtained every predetermined period of time. Next, a force obtained at a time point $t_{03}$ is represented by $f_{03}$, a force obtained at a time point $t_1$ is represented by and a force obtained at a time point $t_{11}$ is represented by $f_{11}$. Next, the reference information generating unit 15 compares $\Delta f_1 = |f_1 - f_{03}|$ and $\Delta f_{11} = |f_{11} - f_1|$ are compared with each other. Next, the reference information generating unit 15 decides whether the difference is the predetermined first threshold value or more. In this example, since the difference is the predetermined threshold value or more, the reference information generating unit 15 sets the time point $t_1$ as a reference point. Then, in a similar manner, the reference information generating unit 15 sequentially sets reference points. The set reference point is represented by a black circle "●" in FIG. 11. Next, the set reference point is generated by the reference information generating unit 15 as reference information obtained by pairing a force with a position every predetermined period of time (for example, every 4 msec) through the use of the timer 10, is output from the reference information generating unit 15 to the database input/output unit 14 together with time, and is stored in the reference information database 22, and by using the input IF 8, the operator gives instructions for ending the generation of reference information. More specifically, in a state in which the tip end of the forceps 2a passes through the abdominal wall 3, is inserted into the body of the living body 4, and is not in contact with the surgery site 5, at the end of movement of the forceps 2a in the predetermined direction, the operator 6 gives to the input IF 8 end instructions of the generation of reference information.

Next, in step S6, the force used in step S5 and detected in step S3 is decided by the force decision unit 12. More specifically, the force decision unit 12 decides whether the force detected by the force detection unit 13 is a predetermined second threshold value (threshold value for load notification) (for example, 2 N) or more. When the force decision unit 12 decides that the force is the predetermined second threshold value or more, the decision result notification unit 17 gives a warning to the operator 6 through the monitor 17a, the loudspeaker 17b, or the like (step S7). Thereafter, furthermore, the force measurement process returns to step S1.

On the other hand, when the force decision unit 12 decides that the force is not the predetermined second threshold value or more in step S6, the force measurement process proceeds to step S8. Steps S6 and S7 are operations to enhance safety. Depending on conditions, when the safety can be secured by another means or the like, steps S6 and S7 may be omitted.

Next, as shown in FIG. 9D, at a time point at which the tip end of the forceps is in contact with the internal organ 5, the force detection unit 13 detects a force acting from outside the body to the forceps 2a (step S8).

Next, the instrument position detection unit 19 detects a position of the forceps 2a from outside the body (step S9).

Next, in step S10, the reference information selecting unit 16 selects reference information for calculating an individual force.

Figure 12A:
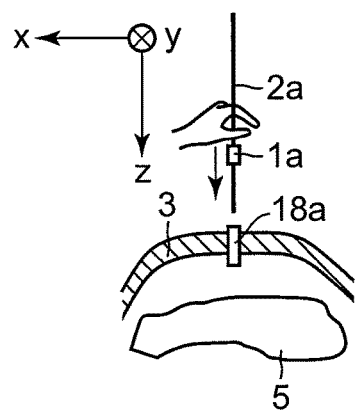
FIG. 12A is a view for describing the operation of the endoscopic surgery in the first embodiment of the present invention.
Figure 12B:
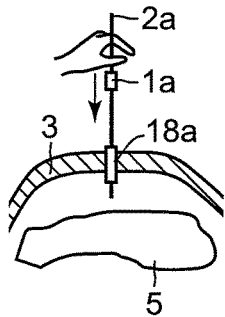
FIG. 12B is a view for describing the operation of the endoscopic surgery in the first embodiment of the present invention.
Figure 12C:
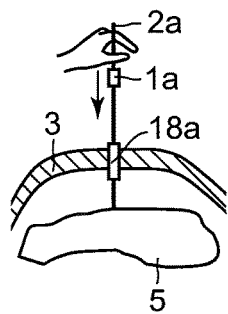
FIG. 12C is a view for describing the operation of the endoscopic surgery in the first embodiment of the present invention.
Figure 13A:
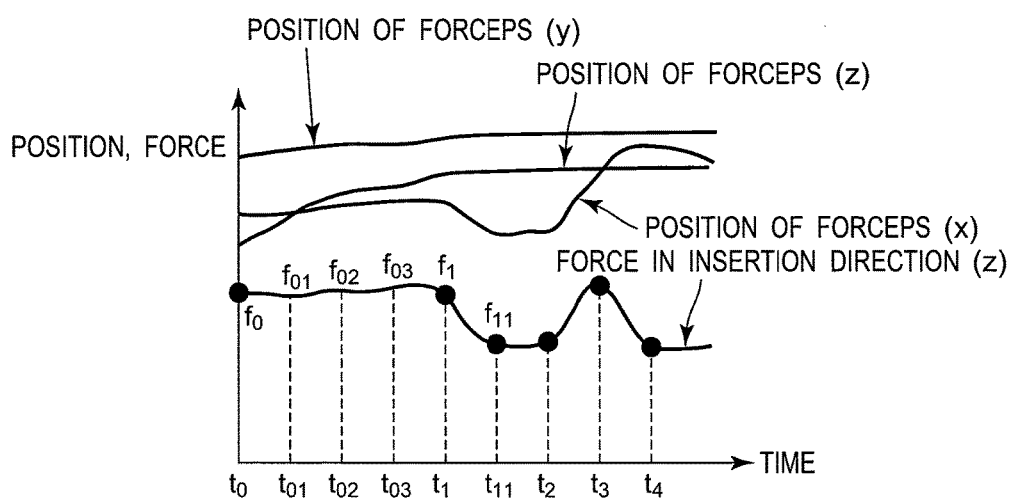
FIG. 13A is a graph showing a relationship between a force in an insertion state and a position of the instrument and time in the first embodiment of the present invention.
Figure 13B:
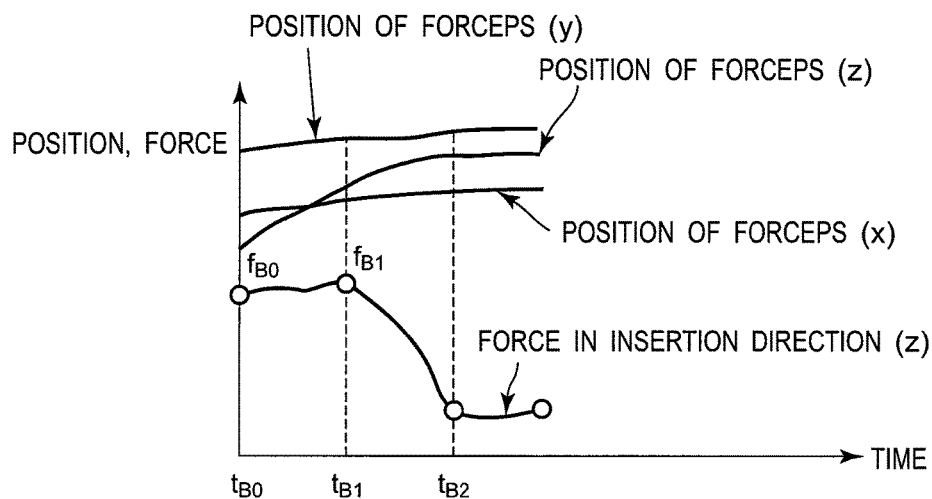
FIG. 13B is a graph showing a relationship between a force in an insertion state and a position of an instrument and time in the first embodiment of the present invention.

FIG. 13A shows a graph of time and a position and a force of the forceps 2a in the reference information generated by the reference information generating unit 15 in step 5. FIG. 13B is a graph of a position and a force of the forceps 2a obtained when the tip end of the forceps 2a is brought into contact with the internal organ 5 as shown in FIGS. 12B and 12C and time.

In step S10, the reference information selecting unit 16 selects reference information closest to the position (however, a position of an axis orthogonal to an insertion direction except for a position in the insertion direction) of the forceps 2a in FIG. 12C.

More specifically, with respect to a force of the forceps 2a in FIG. 12C, a reference point for calculating an individual force is calculated by the calculation unit 11a of the individual force calculation unit 11. As a calculation method, as in the reference information generating unit 15, a time point at which a displacement of the force detected by the force detection unit 13 changes by a predetermined third threshold value (threshold value for setting individual force calculation reference point or threshold value for setting second time point) (for example, 0.1 N) or more is set as an individual force calculation reference point by the calculation unit 11a of the individual force calculation unit 11. The "individual force calculation reference point" mentioned here means a time point serving as a reference to individually calculate (measure) forces that respectively act based on the sum of forces detected by the force detection unit 13. A start time point in FIG. 13B is set as the first reference point by the calculation unit 11a of the individual force calculation unit 11. A reference point set by the calculation unit 11a of the individual force calculation unit 11 is indicated by a white circle "○" in FIG. 13B. Next, every position of the forceps 2a between the reference points in FIG. 13B, except for a position in an insertion direction (z-axis direction in FIGS. 12C and 13B), with respect to a position of an axis (x-axis direction and y-axis direction in FIGS. 12C and 13B) orthogonal to the insertion direction, the reference information in FIG. 13A is compared with reference information at every reference point by the reference information selecting unit 16 of the individual force calculation unit 11. In this example, a position closest to time series information at the position of the forceps 2a in an x direction and a y direction in FIG. 13B is calculated from FIG. 13A by the calculation unit 11a of the individual force calculation unit 11. As an example of a method of calculating the closest position, with respect to a position x of the forceps 2a between a reference point A and a reference point B, a straight line is calculated by a least-square method in the calculation unit 11a of the individual force calculation unit 11, and an inclination and an intercept of the straight line are compared in the reference information selecting unit 16 of the individual force calculation unit 11. By the above method, in the example, the reference information selecting unit 16 of the individual force calculation unit 11 decides that a section from the time point $t_0$ to the time point $t_1$ in FIG. 13A serving as reference information is closest to a section from the time point $t_{B0}$ to the time point $t_{B1}$ in FIG. 13B serving as measurement information.

Thus, reference information to calculate individual forces at time points $t_{B0}$ to $t_{B1}$ in FIG. 13B in the calculation unit 11a of the individual force calculation unit 11 is selected by the reference information selecting unit 16 as the time points $t_0$ to $t_1$ in FIG. 13A. Similarly, pieces of reference information at time points $t_{B1}$ to $t_{B2}$ in FIG. 13B are selected by the reference information selecting unit 16. Thus, since the section from the time point $t_{B1}$ to the time point $t_{B2}$ in FIG. 13B is the same as the section from the time point $t_0$ to the time point $t_1$ in FIG. 13A, reference information to calculate individual forces at the time points $t_{B1}$ to $t_{B2}$ in FIG. 13B in the calculation unit 11a of the individual force calculation unit 11 are selected by the reference information selecting unit 16 as the time points $t_0$ to $t_1$ in FIG. 13A. The ID of the reference information selected by the reference information selecting unit 16 is stored from the reference information selecting unit 16 as an "ID of reference information" of the measurement information database 9 through the database input/output unit 14.

Next, in step S11, based on the reference information selected by the reference information selecting unit 16, the calculation unit 11a of the individual force calculation unit 11 calculates individual forces. A value obtained by subtracting a force calculated based on the force of the reference information selected by the reference information selecting unit 16, from the force of the force detection unit 13 at the time point at which the individual forces are calculated by the calculation unit 11a of the individual force calculation unit 11 is calculated as an individual force by the calculation unit 11a of the individual force calculation unit 11. As an example of the method of calculating the subtracting force, a straight line is calculated by a least-square method in the calculation unit 11a of the individual force calculation unit 11 based on the force of the reference information of the selected section. A force f calculated by the calculation unit 11a of the individual force calculation unit 11 is given by f=a×t×b (a is an inclination, b is an intercept, t is time, and f is a force). By using the straight line, the subtracting force f is calculated by the calculation unit 11a of the individual force calculation unit 11, and the calculated force is subtracted from the force detected by the force detection unit 13, so that an individual force is calculated by the calculation unit 11a of the individual force calculation unit 11.

Figure 13C:
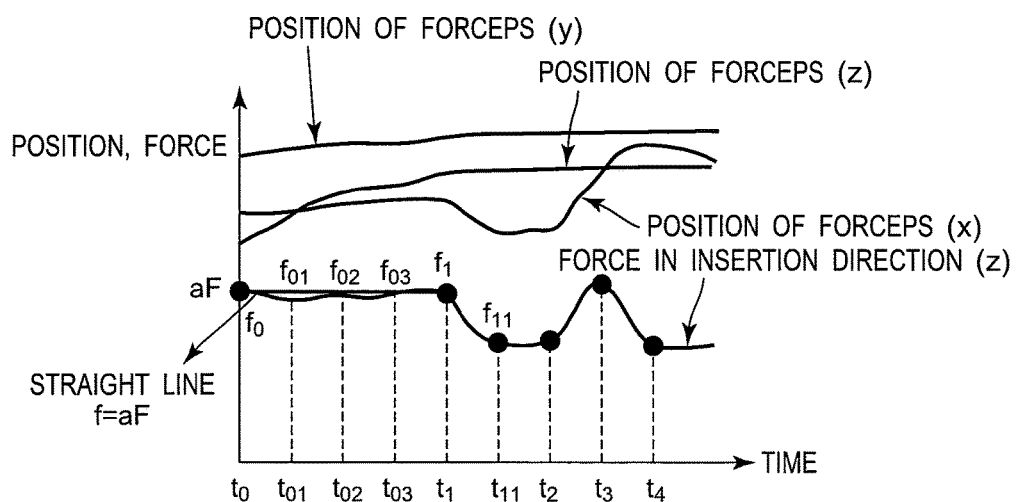
FIG. 13C is a graph showing a relationship between a force in an insertion state and a position of the instrument and time in the first embodiment of the present invention.

An example will be described in detail with reference to FIGS. 13A and 13B. Forces in a section of the reference information (time points $t_0$ to $t_1$ in FIG. 13A) selected in step S10 are given as $f_0, f_{01}, f_{02}, \ldots, f_1$ in FIG. 13A. A straight line is calculated by a least-square method using the forces $f_0, f_{01}, f_{02}, \ldots, f_1$ in the calculation unit 11a of the individual force calculation unit 11. Since inclinations at the time points $t_0$ to $t_1$ in FIG. 13A become zero, a straight line given by f=aF is obtained as shown in FIG. 13C. The time points $t_0$ to $t_1$ in FIG. 13C show displacements of forces on timeseries. Next, individual forces at the time point $t_{B0}$ to the time point $t_{B1}$ in FIG. 13B are defined as values that are obtained by subtracting aF from the forces in the calculation unit 11a of the individual force calculation unit 11. More specifically, when the force at the time point $t_{B0}$ in FIG. 13B is given by $f_{B0}$, an individual force at the time point $t_{B0}$ is given by $f_{B0}$–aF. Similarly, when a force at the time point $t_{B1}$ is given by $f_{B1}$, an individual force at the time point $t_{B1}$ is given by $f_{B1}$–aF. Next, individual forces at the time point $t_{B1}$ to the time point $t_{B2}$ are calculated by the calculation unit 11a of the individual force calculation unit 11. The time point $t_{B1}$ to the time point $t_{B2}$, as shown in FIG. 12C, show states in which the operator 6 gradually strongly brings the forceps 2a into press contact with the internal organ 5. Reference information to calculate the individual forces at the time points $t_{B1}$ to $t_{B2}$ in the calculation unit 11a of the individual force calculation unit 11 is selected in step S10 by the reference information selecting unit 16 as the time points $t_0$ to $t_1$ in FIG. 13A. Similarly, a straight line is calculated by a least-square method based on the forces $f_0, f_{01}, f_{02}, \ldots, f_1$ in the calculation unit 11a of the individual force calculation unit 11. In this example, since f=aF is satisfied as shown in FIG. 13C, the individual forces at the time point $t_{B1}$ to the time point $t_{B2}$ in FIG. 13B are values obtained by subtracting the force aF from the measured force in the calculation unit 11a of the individual force calculation unit 11. In the example, when the force at the time point $t_{B1}$ in FIG. 13B is given by $f_{B1}$, an individual force at the time point $t_{B1}$ is given by $f_{B1}$–aF. Similarly, when a force at the time point $t_{B2}$ is given by $f_{B2}$, an individual force at the time point $t_{B2}$ is given by $f_{B2}$–aF. The individual force calculated by the calculation unit 11a of the individual force calculation unit 11 is output to the database input/output unit 14 together with time and stored in the measurement information database 9.

In step S12, a load of the individual force calculated in step S11 is decided by the force decision unit 12. More specifically, the force decision unit 12 decides whether the individual force calculated in step S11 is a predetermined fourth threshold value (threshold value for load notification) (for example, 2 N) or more. When the force decision unit 12 decides that the calculated individual force is the predetermined fourth threshold value or more, the decision result notification unit 17 gives a warning to the operator 6 through the use of the monitor 17a, the loudspeaker 17b, or the like (load notification is performed) (step S13). Thereafter, furthermore, the force measurement process returns to step S1. On the other hand, when the force decision unit 12 decides that the calculated individual force is not the predetermined fourth threshold value or more in step S12, the force measurement process returns to step S1.

As the first threshold value, the second threshold value, the third threshold value, and the fourth threshold value, different values may be used depending on the types of the internal organs 5 or the surgery sites 5. For example, the first threshold value, the second threshold value, the third threshold value, and the fourth threshold value can be preliminarily selected by the operator 6 from a plurality of threshold values created in advance or can also be input in advance by the operator 6 through an input device such as a keyboard or a button. The second threshold value and the third threshold value used in decision in the force decision unit 12 need to be set in advance as values larger than the first threshold value used in the reference information generating unit 15 and the fourth threshold value used in the reference information selecting unit 16, respectively.

The reference information is stored as a pair of a position and a force of each of the forceps 2a, 2b. However, when the forceps 2a, 2b are inserted in only the direction shown in FIG. 10A, the detection in the instrument position detection unit 19 and the storage of the positions of the forceps 2a, 2b for the reference information may not be performed. In this case, since the insertion in only one direction is performed, only one piece of reference information is generated, and the reference information selecting unit 16 of the individual force calculation unit 11 selects the generated reference information. At this time, more specifically, the operator gives instructions for not-storing the reference information in the reference information generating unit and the measurement information generating unit through the input IF 8. In this case, the reference information selecting unit 16 selects the reference information stored in the reference information database 22 regardless of the present (force measurement-time) positions of the forceps 2a, 2b, and calculates an individual force in the calculation unit 11a of the individual force calculation unit 11 by using the reference information selected by the reference information selecting unit 16.

Figure 10G:
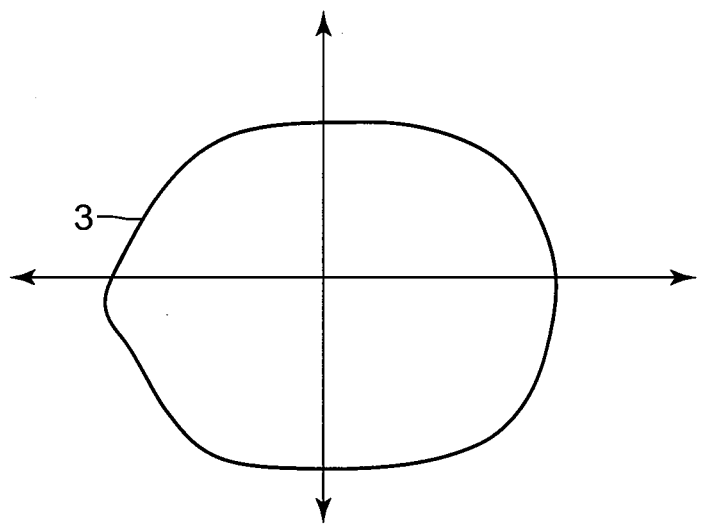
FIG. 10G is a view for describing the operation of the endoscopic surgery in the first embodiment of the present invention.
Figure 10H:
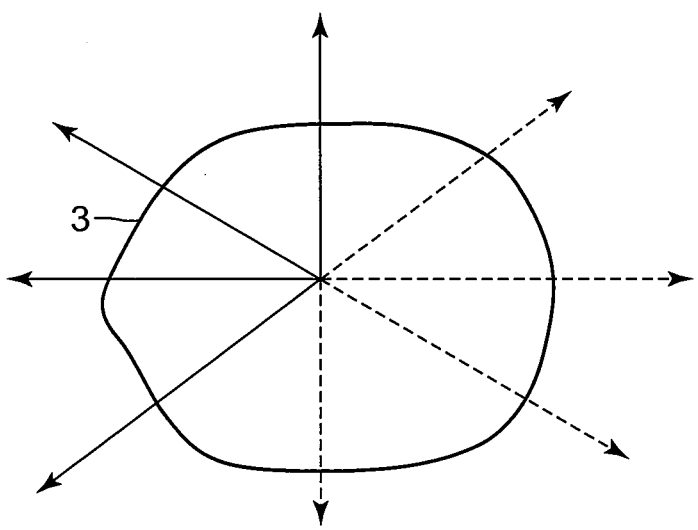
FIG. 10H is a view for describing the operation of the endoscopic surgery in the first embodiment of the present invention.

In the first embodiment, the forceps 2a is operated as shown in FIG. 10F. However, the operation of the forceps 2a is not limited to that shown in FIG. 10F. For example, operating directions of the forceps 2a are defined as four directions as shown in FIG. 10G, or the forceps 2a may be operated in only a direction of a solid line shown in FIG. 10H, and, with respect to a diagonal direction (direction of a dotted line shown in FIG. 10H), a sign may be inverted to automatically generate reference information in the reference information generating unit 15.

Effects of First Embodiment

As described above, by the force detection unit 13 disposed from outside the body, a force generated when the forceps 2a, 2b act on the abdominal wall 3 and forces acting on the tip ends of the forceps 2a, 2b can be individually calculated in the calculation unit 11a of the individual force calculation unit 11. More specifically, forces generated when a surgical instrument acts inside the body can be individually measured from the outside of the body. Furthermore, the individual forces individually calculated in the calculation unit 11a of the individual force calculation unit 11 are decided by the force decision unit 12, and the operator 6 is notified of a decision result, so that force sense that has been achieved by the intuition and the experiences of the operator 6 can be quantified and presented to the operator 6.

Second Embodiment

In a second embodiment, as in the first embodiment, as shown in FIG. 1, there is exemplified force measurement performed when the trocar 18a and 18b are fitted in holes formed in the abdominal wall 5 of the human body 4, respectively, and the forceps 2a and the forceps 2b are inserted into the trocars, respectively.

Figure 14:
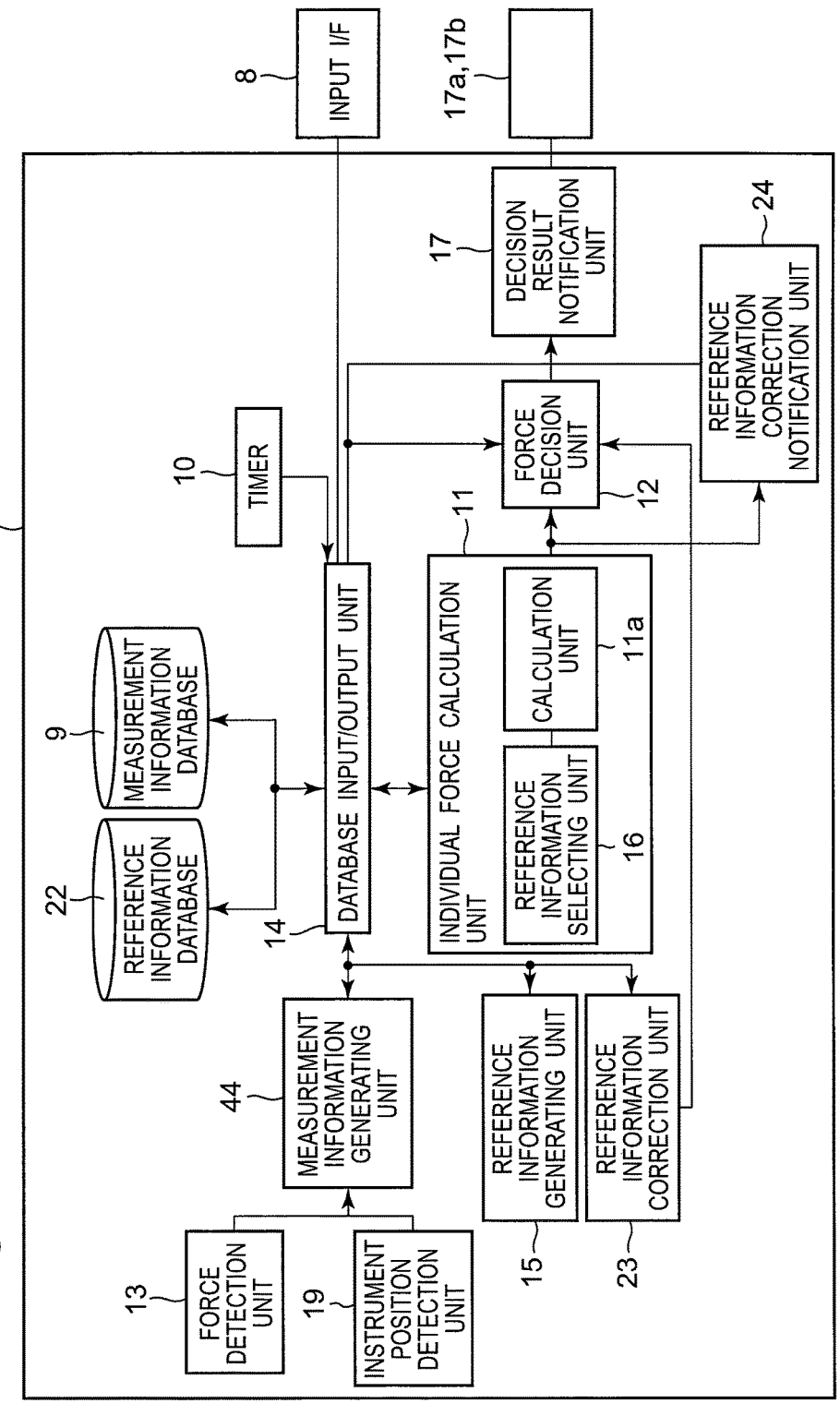
FIG. 14 is a block diagram showing a detailed configuration of a force measurement apparatus according to a second embodiment of the present invention.

FIG. 14 shows a configuration of a force measurement apparatus 1C in the second embodiment.

The force measurement apparatus 1C is obtained by adding a reference information correction notification unit 24 and a reference information correction unit 23 to the force measurement apparatus 1 according to the first embodiment.

In the force measurement apparatus 1C, since a basic configuration including the measurement information database 9, the database input/output unit 14, the force detection unit 13, the instrument position detection unit 19, the reference information generating unit 15, the force decision unit 12, and decision result notification unit 17 is the same as that in the first embodiment, an description of the common parts is omitted, and only different parts will be described below in detail.

—Reference Information Database 22—

The reference information database 22 stores information relating to the force detected by the force detection unit 13 and a position of the forceps 2a detected by the instrument position detection unit 19 before the forceps 2a is brought into contact with the internal organ 5 together with time through the use of the timer 10.

The reference information stored in the reference information database 22 is input/output by the database input/output unit 14.

FIG. 15 shows an example of the contents of the reference information of the reference information database 22.

Since "time", "force", "position", "reference point", and "ID" are the same as those in the first embodiment, a description thereof will be omitted. A "re-creation flag" is a flag representing the presence/absence of correction of reference information in the reference information correction notification unit 24. When the reference information correction notification unit 24 decides that the reference information need to be corrected, the flag is set to "1". When the reference information correction notification unit 24 decides that the reference information need not be corrected, the flag is set to "0".

<<Reference Information Generating Unit 15>>

The reference information generating unit 15, as in the first embodiment, generates reference information serving as information obtained by pairing a position of the forceps 2a before the forceps 2a, 2b pass through the abdominal wall 3 and are brought into contact with the internal organ 5, a value detected by the force detection unit 13, and a reference point (will be described later). The generation of the reference information is started by reference information generation start instructions generated from the input IF 8. The reference information is generated every predetermined period of time (for example, every 4 msec) through the use of the timer 10. The reference information is output with time from the reference information generating unit 15 to the database input/output unit 14 and stored in the reference information database 22. In addition, the reference information generating unit 15 sets the re-creation flag in the reference information database 22 to "0" through the database input/output unit 14.

<<Individual Force Calculation Unit 11>>

The individual force calculation unit 11 causes the calculation unit 11a to calculate an individual force generated when the forceps 2a, 2b are brought into contact with the internal organ 5 based on the reference information and the force detected by the force detection unit 13. The reference information used in the individual force calculation unit 11 is selected by the reference information selecting unit 16 based on the present (force measurement-time) positions of the forceps 2a, 2b. As selecting method by the reference information selecting unit 16, as in the first embodiment, when there is no closest reference information, the reference information selecting unit 16 sets "ID of reference information" of the measurement information database 9 as "−1".

<<Reference Information Correction Notification Unit 24>>

The reference information correction notification unit 24 detects the presence/absence of correction of the reference information and notifies an operator that the reference information need to be corrected. More specifically, the reference information correction notification unit 24, based on an operation of the reference information selecting unit 16, decides whether the reference information stored in the reference information database 22 need to be corrected. When the reference information correction notification unit 24 decides that the reference information need to be corrected, the reference information correction notification unit 24 notifies the operator 6 that the reference information need to be corrected. When the reference information selecting unit 16 of the individual force calculation unit 11 cannot select the reference information, the reference information correction notification unit 24 decides that the reference information need to be corrected to notify the operator that the reference information need to be corrected. More specifically, in the reference information selecting unit 16 of the individual force calculation unit 11, when the reference information correction notification unit 24 decides that close reference information cannot be selected, i.e., when the reference information correction notification unit 24 decides that "−1" is set as the "ID of reference information" of the measurement information database 9, the reference information correction notification unit 24 decides that the reference information need to be corrected. When the reference information correction notification unit 24 decides that the sign of the individual force calculated by the calculation unit 11a of the individual force calculation unit 11 is different from the sign of the force detected by the force detection unit 13 used in calculation of the individual force, the reference information correction notification unit 24 decides that the reference information need to be corrected. When the reference information correction notification unit 24 decides that the reference information need to be corrected, the reference information correction notification unit 24 stores "1" as the "re-creation flag" of the reference information database 22 through the database input/output unit 14, and the reference information correction notification unit 24 notifies the operator 6. The reference information correction notification unit 24 notifies the operator 6 such that it is displayed on a monitor 18a that re-creation is required, or a warning sound is made through the loudspeaker 17b. When the reference information correction notification unit 24 decides that the sign of the individual force calculated by the calculation unit 11a of the individual force calculation unit 11 is the same as the sign of the force detected by the force detection unit 13 used in calculation of the individual force, the reference information correction notification unit 24 decides that the reference information need not be corrected, and then, the reference information correction notification unit 24 sets "0" as the "re-creation flag" of the reference information database 22.

<<Reference Information Correction Unit 23>>

The reference information correction unit 23 corrects reference information based on a notice from the reference information correction notification unit 24. More specifically, the reference information correction unit 23 receives the notice from the reference information correction notification unit 24 or corrects the reference information in response to instructions from the operator 6.

The reference information is corrected such that the reference information is generated by the same method as that in the reference information generating unit according to the first embodiment in the reference information correction unit 23, and all the contents of the reference information database 22 are replaced by the reference information correction unit 23. The reference information correction unit 23 may generate only a position where the "re-creation flag" of the reference information is "1", and the reference information correction unit 23 may replace the generated position. Upon completion of the generation, the reference information correction unit 23 sets "0" as a "re-creation flag".

Figure 16:
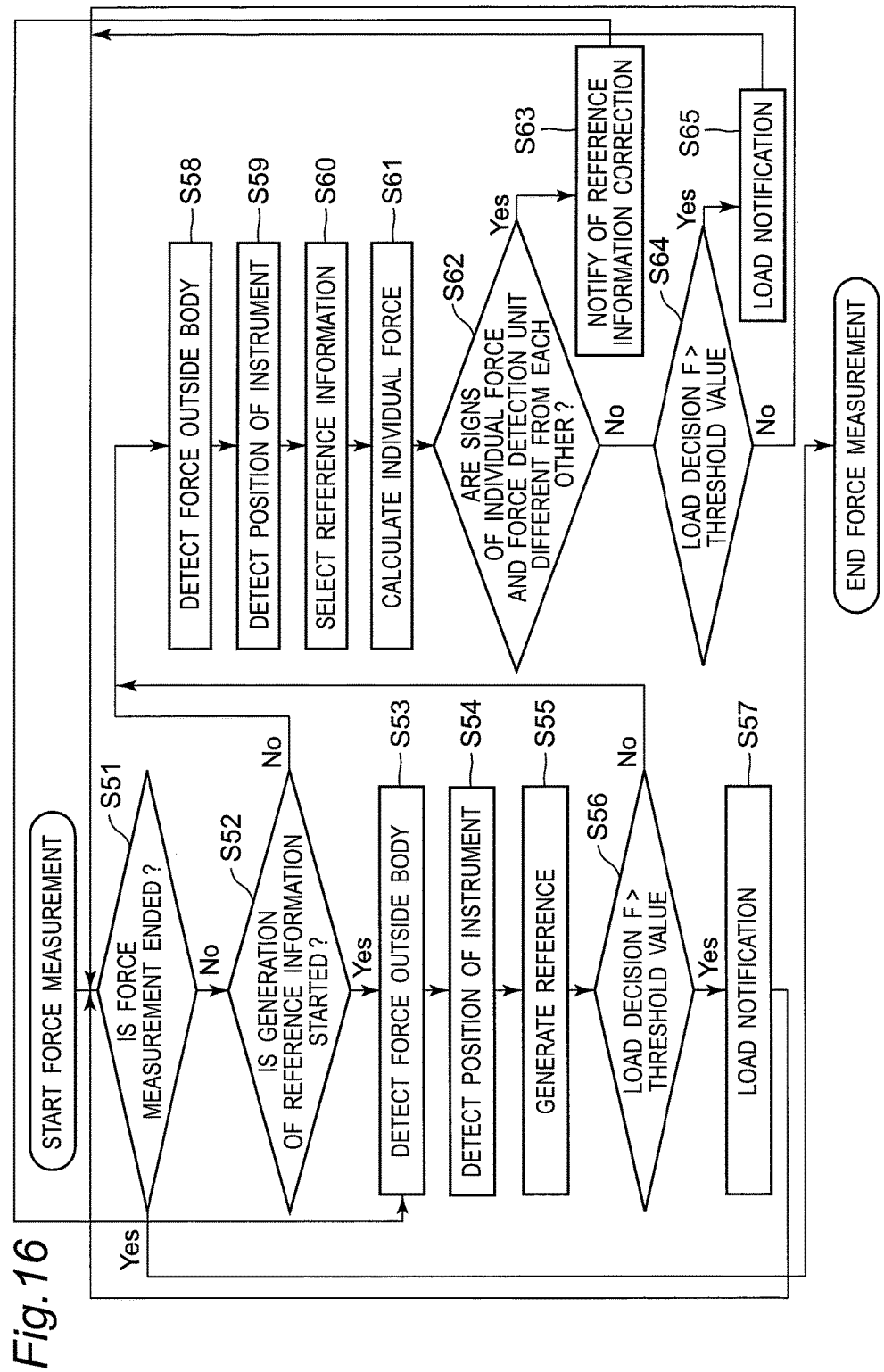
FIG. 16 is a flow chart of the force measurement apparatus according to the second embodiment of the present invention.
Figure 17A:
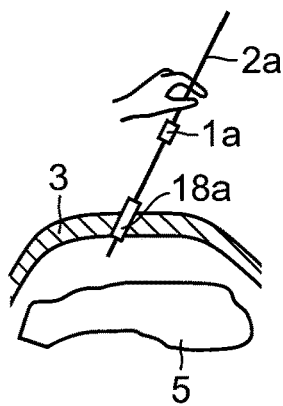
FIG. 17A is a view for describing an operation of endoscopic surgery in the second embodiment of the present invention.
Figure 17B:
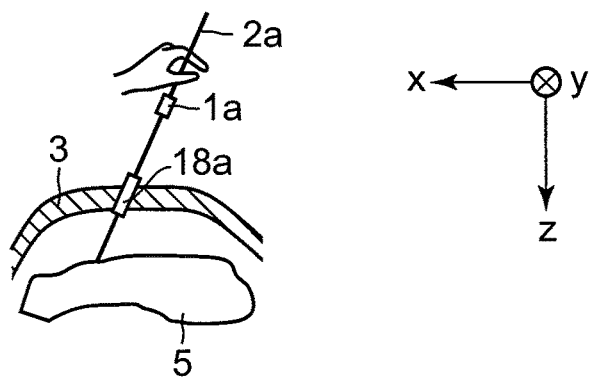
FIG. 17B is a view for describing the operation of the endoscopic surgery in the second embodiment of the present invention.

Operational steps of a force measurement process in the force measurement apparatus 1C according to the second embodiment will be described below. FIG. 16 is a flow chart of the force measurement apparatus 1C according to the second embodiment. In this case, as shown in FIGS. 17A and 17B, a task in which the forceps 2a is tilted and inserted into the human body 4 in a downward direction from above the human body 4 will be exemplified.

First, when receiving start instructions for force measurement via the input IF 8, the force measurement apparatus 1C starts force measurement.

First, in step S51, when receiving end instructions for force measurement via the input IF 8, the force measurement apparatus 1C ends the force measurement. When the end instructions for force measurement are not input, the force measurement process proceeds to next step S52.

Next, in step S52, when generation start instructions for reference information are input via the input IF 8, the force measurement process proceeds to step S53. When generation start instructions for reference information are not input, the force measurement process proceeds to step S58.

Next, in step S53, the force detection unit 13 detects a force acting on the forceps 2a serving as an example of an instrument, from outside the body.

Next, in step S54, the instrument position detection unit 19 detects a position of the forceps 2a from outside the body.

Next, in step S55, the reference information generating unit 15 generates reference information by calculating a reference point based on the force detected in step S53 and the position of the forceps 2a detected in step S54. Although the generating method is the same as that in step S5 in the first embodiment, "0" is set as the "re-creation flag" in the reference information generating unit 15. FIG. 11 shows a graph of the generated reference information.

In step S56, the force used in step S55 and detected in step S53 is decided by the force decision unit 12. More specifically, the force decision unit 12 decides whether the force detected by the force detection unit 13 is a predetermined fifth threshold value (threshold value for deciding load) (for example, 2 N) or more. When the force decision unit 12 decides that the force is the predetermined fifth threshold value or more, the decision result notification unit 17 gives a warning to the operator 6 through the monitor 17a, the loudspeaker 17b, or the like (step S57). Thereafter, furthermore, the force measurement process returns to step S51. When the force decision unit 12 decides that the force is not the predetermined fifth threshold value or more in step S56, the force measurement process proceeds to step S58.

Next, as shown in FIG. 17B, at a time point at which the tip end of the forceps is in contact with the internal organ 5, the force detection unit 13 detects a force acting from outside the body to the forceps 2a (step S58).

Next, the instrument position detection unit 19 detects a position of the forceps 2a from outside the body (step S59).

In step S60, the reference information selecting unit 16 selects reference information to calculate an individual force.

Figure 18A:
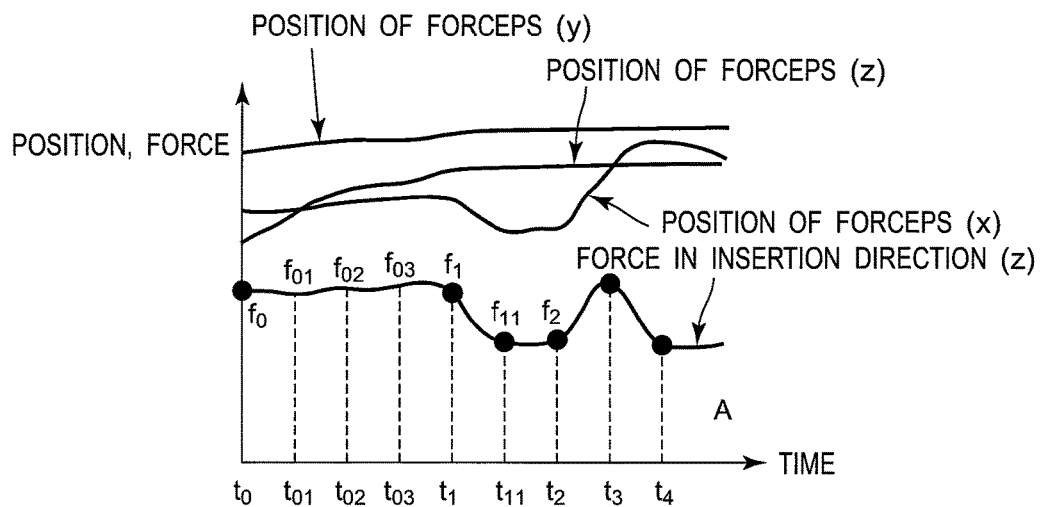
FIG. 18A is a graph showing a relationship between a force in an insertion state and a position of an instrument and time in the second embodiment of the present invention.
Figure 18B:
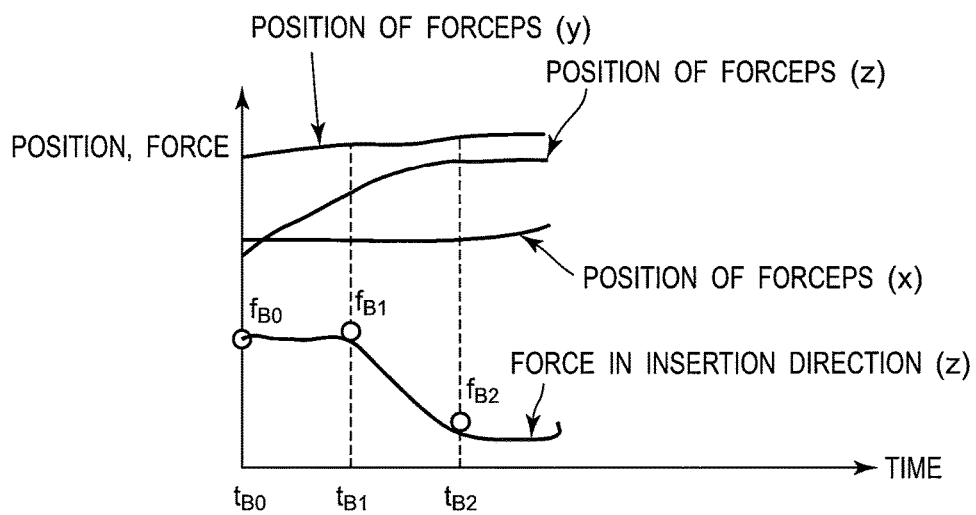
FIG. 18B is a graph showing a relationship between a force in an insertion state and a position of the instrument and time in the second embodiment of the present invention.

FIG. 18A shows a graph showing a relationship among a force, a position of the instrument, and time upon insertion in the reference information generated by the reference information generating unit 15 in step S55. FIG. 18B is a graph of a position and a force of the forceps 2a and time obtained when the tip end of the forceps 2a is brought into contact with the internal organ 5 as shown in FIGS. 17A and 17B.

The reference information selecting unit 16, as in the first embodiment, selects reference information closest to the position (however, a position of an axis orthogonal to an insertion direction except for a position in the insertion direction) of the forceps 2a in FIG. 17B.

More specifically, first, with respect to a force of the forceps 2a in FIG. 17B, a reference point is calculated by the calculation unit 11a of the individual force calculation unit 11. As a calculation method, as in the reference information generating unit 15, a time point at which a displacement of the force detected by the force detection unit 13 changes by a predetermined sixth threshold value (threshold value for setting reference point) (for example, 0.1 N) or more is set as an individual force calculation reference point by the calculation unit 11a of the individual force calculation unit 11. The "individual force calculation reference point" mentioned here means a point (time point) serving as a reference to individually calculate forces that respectively act based on the sum of forces detected by the force detection unit 13. A start time point in FIG. 17B is set as the first reference point by the calculation unit 11a of the individual force calculation unit 11. A reference point set by the calculation unit 11a of the individual force calculation unit 11 is indicated by a white circle "○" in FIG. 17B. Next, every position of the forceps 2a between the reference points in FIG. 17B, except for a position in an insertion direction (z-axis direction in FIG. 17B), a position of an axis (x-axis direction and y-axis direction in FIG. 17B) orthogonal to the insertion direction, is compared with the reference information in FIG. 18A at every reference point by the reference information selecting unit 16. A comparing method is the same as that in the first embodiment, it is calculated by the calculation unit 11a of the individual force calculation unit 11 that a section from a time point $t_{11}$ to a time point $t_2$ in FIG. 18A is the same as a section from time points $t_{B0}$ to $t_{B1}$ in FIG. 18B.

Thus, reference information to calculate individual forces at time points $t_{B0}$ to $t_{B1}$ in FIG. 18B in the calculation unit 11a of the individual force calculation unit 11 is selected by the reference information selecting unit 16 as the time points $t_{11}$ to $t_2$ in FIG. 18A. Similarly, pieces of reference information at time points $t_{B1}$ to $t_{B2}$ are selected by the reference information selecting unit 16. Thus, since the section from the time point $t_{B1}$ to the time point $t_{B2}$ in FIG. 18B is the same as the section from the time point $t_{11}$ to the time point $t_2$ in FIG. 13A, reference information to calculate individual forces at the time points $t_{B1}$ to $t_{B2}$ in FIG. 18B in the calculation unit 11a of the individual force calculation unit 11 are selected by the reference information selecting unit 16 as the time points $t_{11}$ to $t_2$ in FIG. 18A. The ID of the reference information selected by the reference information selecting unit 16 is stored from the reference information selecting unit 16 as an "ID of reference information" of the measurement information database 9 through the database input/output unit 14.

Figure 17C:
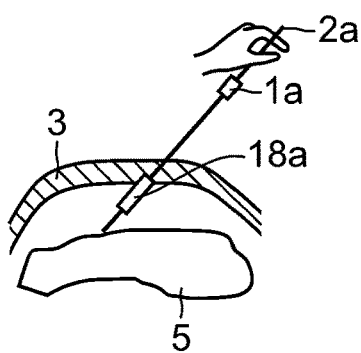
FIG. 17C is a view for describing the operation of the endoscopic surgery in the second embodiment of the present invention.

When the forceps 2a is further tilted as shown in FIG. 17C, there may be no information close to the reference information that has been generated. In this case, the reference information selecting unit 16 sets "−1" as the "ID of reference information".

Next, in step S61, based on the selected reference information, individual forces are calculated by the calculation unit 11a of the individual force calculation unit 11. More specifically, the forces in the section of the reference information (time points $t_{11}$ to $t_2$ in FIG. 18A) selected in step S60 are given as forces $f_{11}$ and $f_2$, respectively. As in the first embodiment, a straight line is calculated by a least-square method based on the forces $f_{11}$ and $f_2$ in the calculation unit 11a of the individual force calculation unit 11, and a force is calculated by the straight line in the calculation unit 11a of the individual force calculation unit 11 (the calculated force is represented by aF).

Individual forces at the time point $t_{B0}$ to the time point $t_{B1}$ in FIG. 18B are defined as values that are obtained by subtracting aF from the measured forces in the calculation unit 11a of the individual force calculation unit 11. More specifically, when the force at the time point $t_{B0}$ in FIG. 18B is given by $f_{B0}$, an individual force $f_{i0}$ at the time point $t_{B0}$ is given by $f_{i0}=f_{B0}-aF$. Similarly, when a force at the time point $t_{B1}$ is given by $t_{B1}$, an individual force $f_{i1}$ at the time point $t_{B1}$ is given by $f_{i1}=f_{B1}-aF$. Next, individual forces at the time point $t_{B1}$ to the time point $t_{B2}$ are calculated by the calculation unit 11a of the individual force calculation unit 11. The time point $t_{B1}$ to the time point $t_{B2}$, as shown in FIG. 17B, show states in which the forceps 2a is gradually strongly brought into press contact with the internal organ 5. Reference information to calculate the individual forces at the time points $t_{B1}$ to $t_{B2}$ in the calculation unit 11a of the individual force calculation unit 11 is selected in step S60 by the reference information selecting unit 16 as the time points $t_{11}$ to $t_2$ in FIG. 18A. Similarly, the force aF to be subtracted from the forces $f_{11}$ and $f_2$ is calculated by the individual force calculation unit 11. Next, individual forces at the time point $t_{B1}$ to the time point $t_{B2}$ in FIG. 18B are defined as values that are obtained by subtracting aF from the calculated forces in the calculation unit 11a of the individual force calculation unit 11. More specifically, when a force at the time point $t_{B1}$ in FIG. 18B is given by $f_{B1}$, the $f_{i1}$ at the time point $t_{B1}$ is given by $f_{i1}=f_{B1}-aF$. Similarly, when a force at the time point $t_{B2}$ is given by $f_{B2}$, an individual force $f_{i2}$ at the time point $t_{B2}$ is given by $f_{i2}=f_{B2}-aF$. The individual force calculated by the calculation unit 11a of the individual force calculation unit 11 is output to the database input/output unit 14 together with time by the calculation unit 11a of the individual force calculation unit 11 and stored in the measurement information database 9.

In step S62, the reference information correction notification unit 24 decides whether the reference information need to be corrected.

When the close reference information cannot be selected by the reference information selecting unit 16 in the calculation unit 11a of the individual force calculation unit 11, i.e., when the reference information correction notification unit 24 decides that "−1" is set as the "ID of reference information" of the measurement information database 9, the reference information correction notification unit 24 decides that the reference information need to be corrected. When the reference information correction notification unit 24 decides that the sign of the individual force calculated by the calculation unit 11a of the individual force calculation unit 11 is different from the sign of the force detected by the force detection unit 13 used in calculation of the individual force, the reference information correction notification unit 24 decides that the reference information need to be corrected. When the reference information correction notification unit 24 decides that the reference information need to be corrected, the reference information correction notification unit 24 stores "1" as the "re-creation flag" of the reference information database 22 through the database input/output unit 14.

For example, in a case where reference information is generated in the state shown in FIG. 17A, when the forceps is further tilted as shown in FIG. 17C, the reference information selecting unit 16 of the individual force calculation unit 11 cannot select close reference information. In this case, the reference information correction notification unit 24 decides that the reference information need to be corrected.

During a surgical operation performed by causing a force to act on the abdominal wall 3 as shown in FIG. 17B, the abdominal wall 3 loosens, and only a force weaker than that obtained when reference information is generated may act. In this case, since a sum of forces detected by the force detection unit 13 used in calculation by the individual force calculation unit becomes weak, when the force of the reference information previously generated is subtracted from the sum of forces in the calculation unit 11a of the individual force calculation unit 11, individual forces become zero or signs thereof are inverted. In this case, the reference information correction notification unit 24 need to correct the reference information.

In step S61, an individual force is calculated by the calculation unit 11a of the individual force calculation unit 11 such that the individual force $f_{i0}$ at the time point $t_{B0}$ is given by $f_{i0}=f_{B0}-aF$, an individual force is calculated by the calculation unit 11a of the individual force calculation unit 11 such that the individual force $f_{i1}$ at the time point $t_{B1}$ is given by $f_{i1}=f_{B1}-aFB$, and an individual force is calculated by the calculation unit 11a of the individual force calculation unit 11 such that the individual force $f_{i2}$ at the time point $t_{B2}$ is given by $f_{i2}=f_{B2}-aF$. For example, the reference information correction notification unit 24 compares the sign of the individual force $f_{i0}$ with the sign of the force $f_{B0}$ detected by the force detection unit 13. When the reference information correction notification unit decides that the signs are equal to each other, the force measurement process proceeds to step S64. When the reference information correction notification unit 24 decides that the signs are different from each other, the reference information correction notification unit 24 decides that the reference information need to be corrected, the reference information correction notification unit 24 stores "1" as the "re-creation flag" of the reference information database 22 through the database input/output unit 14, and the force measurement process proceeds to step S63. The individual forces $f_{i1}$ and $f_{i2}$ are decided by the reference information correction notification unit 24 as described above.

When the reference information correction notification unit 24 decides in step S62 that the reference information need to be corrected, the reference information correction notification unit 24 notifies the operator 6 that the reference information need to be corrected (step S63). Thereafter, in order to correct the reference information, the force measurement process returns to step S51, and the reference information is generated by the reference information generating unit 15.

When the reference information correction notification unit 24 decides in step S62 that the reference information need not be corrected, the force decision unit decides in step S64 a load of the individual force calculated in step S61. More specifically, the force decision unit 12 decides whether the previously calculated individual force is a predetermined seventh threshold value (threshold value for deciding an individual force load) (for example, 0.5 N) or more. When the force decision unit 12 decides that the previously calculated individual force is the predetermined seventh threshold value or more, the decision result notification unit 17 gives a warning to the operator 6 through the monitor 17a, the loudspeaker 17b, or the like (step S65). When the force decision unit 12 decides that the previously calculated individual force is not the predetermined seventh threshold value or more in step S64, the force measurement process returns to step S51.

As the fifth threshold value, the sixth threshold value, and the seventh threshold value, different values may be used depending on the types of the internal organs 5 or the surgery sites 5. For example, the fifth threshold value, the sixth threshold value, and the seventh threshold value can be preliminarily selected by the operator 6 from a plurality of threshold values created in advance or can also be input in advance by the operator 6 through an input device such as a keyboard or a button.

Effects of Second Embodiment

As described above, when the forces obtained by causing the forceps 2a, 2b to act on the abdominal wall 3 and the forces acting on the tip ends of the forceps 2a, 2b are detected by the force detection unit 13 disposed outside the body and individually calculated by the calculation unit 11a of the individual force calculation unit 11, when the reference information cannot be selected by the reference information selecting unit 16 or when the abdominal wall 3 loosens to prevent the previously generated reference information from being used, the reference information correction notification unit 24 decides the necessity of correction of the reference information. When the reference information correction notification unit 24 decides that the reference information need to be corrected, the reference information correction notification unit 24 can notify the operator 6.

Furthermore, the operator 6 receives a notice of the presence/absence of correction of the reference information from the reference information correction notification unit 24, and, when the correction is necessary, the reference information can be corrected by the reference information correction unit 23.

Third Embodiment

Figure 19:
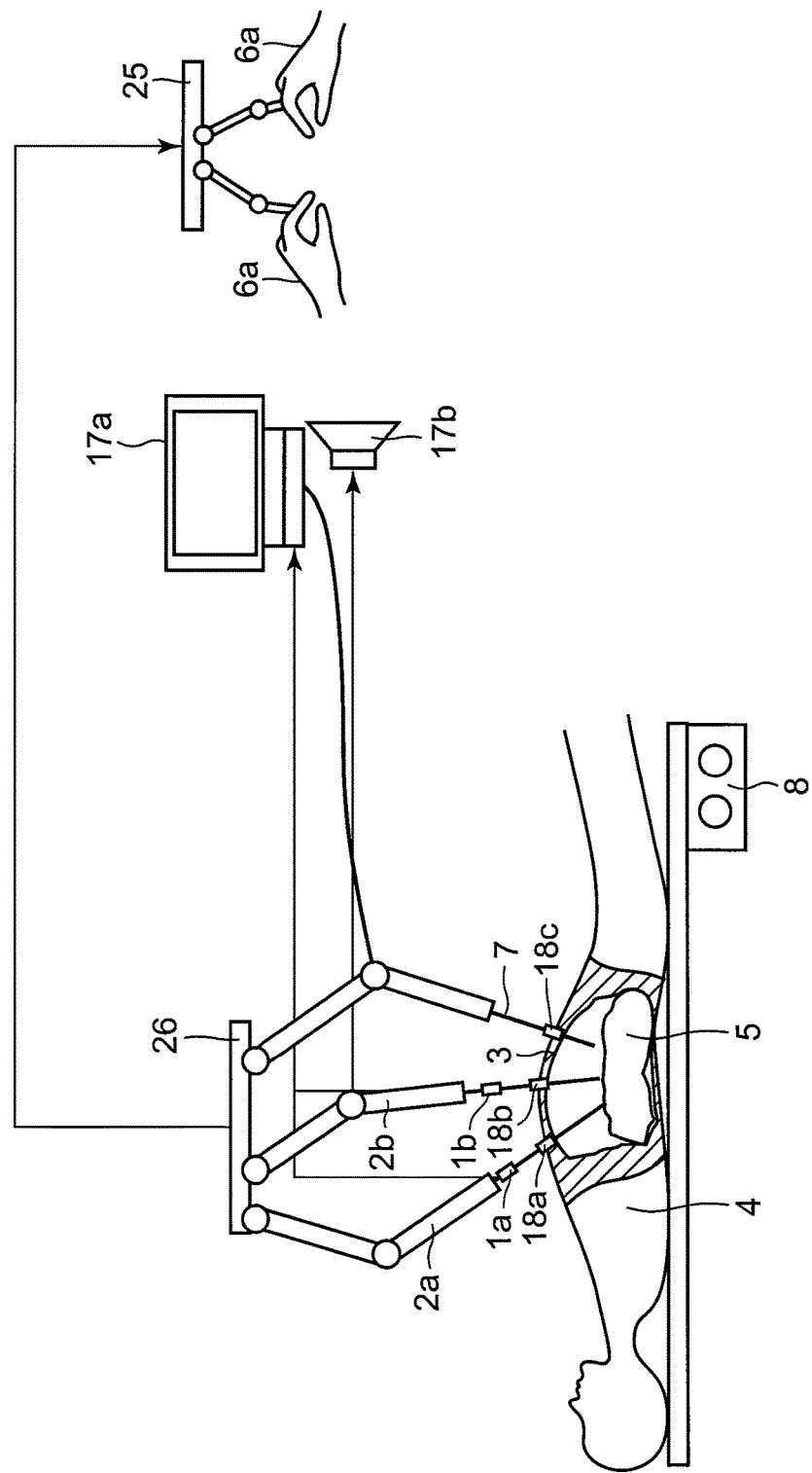
FIG. 19 is a view showing an outline of a configuration of a master-slave device according to a third embodiment of the present invention.

In a third embodiment, as shown in FIG. 19, a case in which endoscopic surgery is performed through the use of a master-slave device 100 using the force measurement apparatus 1 or 1C (in this case, as a typical example, the force measurement apparatus 1 (1a, 1b)) will be exemplified.

An outline of the master-slave device 100 according to a third embodiment of the present invention will now be described. When the operator 6 operates a master robot 25 while checking a video image photographed by the endoscope 7 through the monitor 17a, a slave robot 26 that grips the forceps 2a, 2b or the endoscope 7 operates. The force measurement apparatuses 1a, 1b individually measure a force acting on the abdominal wall 3 or forces acting on the tip ends of the forceps 2a, 2b from outside the body. The forces measured by the force measurement apparatuses 1a, 1b are fed back from the slave robot 26 to the master robot 25, so that the operator 6 can operate the slave robot 26 with an operational feeling as if the operator 6 directly operates the forceps 2a, 2b. The start and end instructions of force measurement of each of the force measurement apparatuses 1a, 1b are given in conjunction with the start and the stop of an inserting task of the slave robot 26 through operating the master robot 25.

Figure 20:
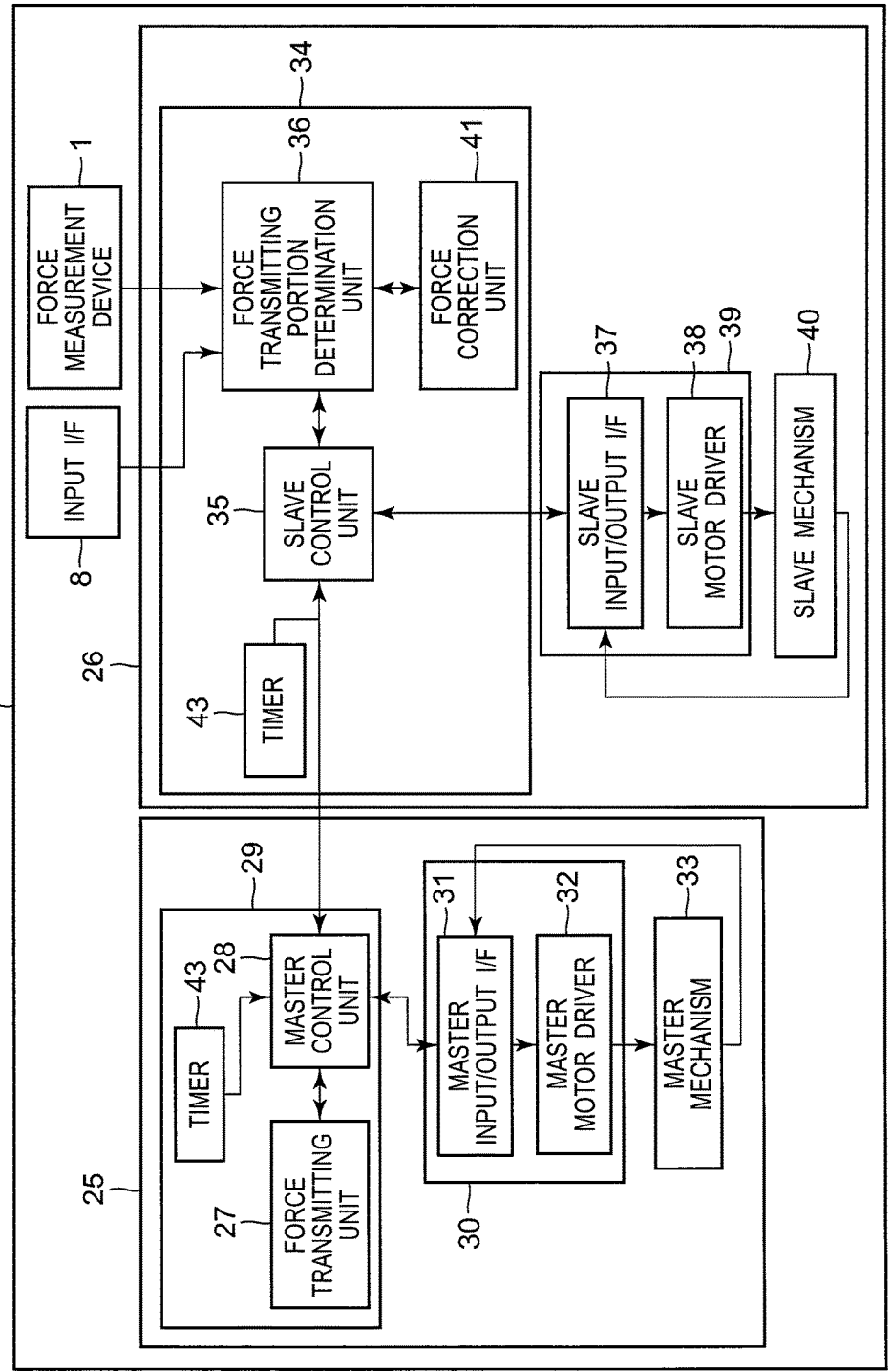
FIG. 20 is a block diagram showing a detailed configuration of the master-slave device according to the third embodiment of the present invention.

Details of the force measurement apparatus 1, the master robot 25, and the slave robot 26 according to the third embodiment will now be described. FIG. 20 is a block diagram of the force measurement apparatus 1, the master robot 25, and the slave robot 26.

<<Master-Slave Device 100, Master Robot 25, and Slave Robot 26>>

The master-slave device 100 is a whole device in the third embodiment of the present invention, and a device that can be remote-controlled by the operator 6 in the task. The master robot 25 is a robot system to be operated such that the operator 6 is in direct contact with the robot system. The slave robot 26 is a robot system that is located at a position distant from the master robot 25 and performs an actual task.

<<Master Mechanism 33 and Slave Mechanism 40>>

A master mechanism 33 is a robot operated such that the operator 6 is in direct contact with the robot, and acquires position information obtained at every sample time at which the operator 6 operates the robot and outputs the position information to a master input/output IF 31. A slave mechanism 40 is a robot that performs a task to insert the forceps 2a, 2b into the body and operates so as to follow the position information acquired by the master mechanism 33.

<<Timer 43>>

A timer 43 is connected to a master control unit 28 and a slave control unit 35, and, after a predetermined period of time (for example, every 1 msec) has elapsed, executes the master control unit 28 or the slave control unit 35. In FIG. 20, although two timers 43 are disposed, the present disclosure is not limited to the configuration. One timer 43 may be connected to both the master control unit 28 and the slave control unit 35.

<<Master Peripheral Device 30 and Slave Peripheral Device 39>>

A master peripheral device 30 transmits information between the master mechanism 33 and a master control device 29. A slave peripheral device 39 also transmits information between the slave mechanism 40 and a slave control device 34. In this case, the master peripheral device 30 includes the master input/output IF 31 and a master motor driver 32. The slave peripheral device 39 includes a slave input/output IF 37 and a slave motor driver 38.

The master input/output IF 31 receives position information from the master mechanism 33 and outputs the position information to the master control unit 28 of the master control device 29. The position information from the master control unit 28 is output to the master motor driver 32 every predetermined period of time (for example, every 1 msec) through the use of the timer 43 through the master input/output IF 31. The master motor driver 32 receives the position information from the master input/output IF 31 and operates motors (not shown) disposed at joint portions connecting a plurality of links of the master mechanism 33 so as to follow the position information, resulting in operating the master mechanism 33.

The slave input/output IF 37 receives the position information from the slave control unit 35 and outputs the position information to the slave motor driver of the slave peripheral device 39. The position information from the slave mechanism 40 is output to the slave control unit 35 every predetermined period of time (for example, every 1 msec) through the use of the timer 43 through the slave input/output IF 37. The slave motor driver 38 receives the position information from the slave input/output IF 37 of the slave peripheral device 39 and operates motors (not shown) disposed at joint portions connecting a plurality of links of the slave mechanism 40 so as to follow the position information, resulting in operating the slave mechanism 40.

<<Master Control Device 29 and Slave Control Device 34>>

The master control device 29 includes the master control unit 28, the force transmitting unit 27, and the timer 43. The master control device 29 has two roles to cause the master mechanism 33 to output moving position information to the slave control device 34 every predetermined period of time (for example, every 1 msec) through the use of the timer 43 and to transmit force information input from the slave control device 34 to the operator 6. The operator 6 operates the master mechanism based on the information of the force of a force transmitting unit 27, and the master control unit 28 converts operation information of the master mechanism 33 into an electric signal. More specifically, the master control unit 28 outputs the position information of the master mechanism 33 from the master input/output IF 31 to the slave control unit 35 every predetermined period of time (for example, every 1 msec) through the use of the timer 43. The force information from the slave control unit 35 is output to the force transmitting unit 27 through the master control unit 28.

The force transmitting unit 27 transmits the information of the force corrected by a correction unit 41 (will be described later) to the operator 6 according to the master mechanism 33. More specifically, the force transmitting unit 27 force-controls the slave mechanism 33 through the slave control unit 35 by using the force information from the slave control unit 35 as a desired value to transmit the information to a hand of the operator 6. As a direction in which a force is generated, one axis in the insertion direction of the master mechanism 33 is used. However, 3 axes in the insertion direction and directions perpendicular thereto, or 6 axes obtained by adding rotating axes to the 3 axes may be used.

The slave control device 34 includes the slave control unit 35, a force transmitting portion determination unit 36, the timer 43, and the force correction unit 41. The slave control device 34 has two roles: to cause the slave mechanism 40 to follow the position information from the master control device 29; and to determine a force transmitted to the master control device 29 in a force transmitting portion detecting unit 36 based on the force information acquired in the force measurement apparatus 1, correct the determined force by the force correction unit 41, and output the corrected force to the master control device 29 as force information. The force measurement apparatuses 1a, 1b, as shown in FIG. 19, are disposed on the tip end side of the forceps 2a, 2b and outside the body near a position where the slave robot 26 is disposed. The slave control unit 35 is connected to the slave mechanism and the master control unit 28 through the slave peripheral device 39, and outputs a control signal that transmits operation information of the master mechanism 33 transmitted from the master control unit 28 to the slave mechanism 40. Based on the control signal transmitted from the slave control unit 35, the slave mechanism 40 is operated to perform a slave operation.

<<Force measurement apparatus 1>>

Each of the force measurement apparatuses 1a, 1b has a function equivalent to that of the force measurement apparatus 1 according to the first embodiment or the second embodiment. From each of the force measurement apparatuses 1a, 1b, an output value from the force detection unit 13, an individual force calculated by the calculation unit 11a of the individual force calculation unit 11, and a decision result obtained in the force decision unit 12 are output to the force transmitting portion determination unit 36 (will be described later).

<<Force Transmitting Portion Determination Unit 36>>

The force transmitting portion determination unit 36 determines a force transmitted from the slave mechanism 40 to the master mechanism 33 based on the information of the force calculated by the force measurement apparatus 1. More specifically, the force transmitting portion determination unit 36, based on a determination flag held therein, determines a force to be transmitted to the master control device 29 from the individual forces determined by the force measurement apparatuses 1a, 1b and the force detected by the force detection unit 13. As the determination flag, "0" is set by the force transmitting portion determination unit 36 when the force detected by the force detection unit 13 is transmitted, and "1" is set by the force transmitting portion determination unit 36 when the individual force calculated by the force measurement apparatus 1 is transmitted. The determination flag may be determined by the operator 6 through the input IF 8. When the force decision unit 12 of the force measurement apparatus 1 decides that a load is applied, a force acting on the load may be transmitted.

<<Force Correction Unit 41>>

The force correction unit 41 corrects a force when the force is switched to the force determined by the force transmitting portion determination unit 36. More specifically, the force correction unit 41 corrects a value of a force output from the force transmitting portion determination unit 36 to the slave control unit 35 such that smoothing is performed to smoothly switch a force set before the switching to a force set after the switching to prevent forces from being quickly changed when the determination flags are switched in the force transmitting portion determination unit 36.

Figure 21:
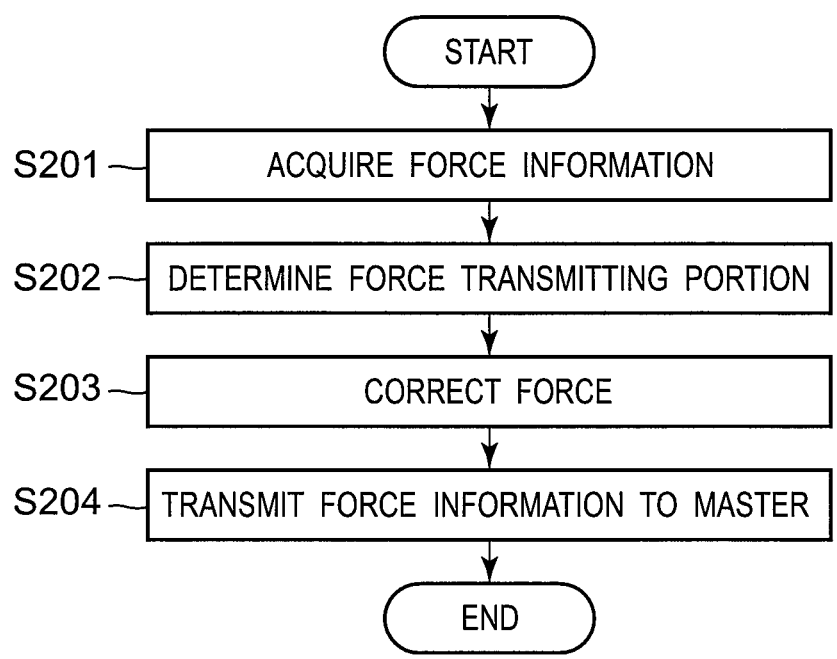
FIG. 21 is a flow chart of an operating procedure of the master-slave device according to the third embodiment of the present invention.

An operating procedure of the master-slave device 100 according to the third embodiment will be described with reference to the flow chart in FIG. 21. In FIG. 21, a description will be given of a procedure performed when the operator 6 directly operates the master mechanism 33 to operate the slave mechanism 40 and to bring the tip ends of the forceps 2a, 2b on the inner side of the body into contact with the internal organ 5 when the forceps 2a, 2b are inserted into the body.

First, in step S201, in a case where the tip ends of the forceps 2a, 2b on the inner side of the body are brought into contact with the internal organ 5 when the forceps 2a, 2b are inserted into the body, pieces of force information are detected by the individual forces calculated by the force measurement apparatuses 1 and the force detected by the force detection unit 13, and are output to the force transmitting portion determination units 36, respectively.

Next, in step S202, the force transmitting portion determination unit 36, when the determination flag held therein is "0", determines that the force of the force detection unit 13 is transmitted to the slave control unit 35. When the determination flag held in the force transmitting portion determination unit 36 is "1", a determination is made such that the individual force calculated by the force measurement apparatus 1 is transmitted to the slave control unit 35. When the determination flag is "0", since the force of the force detection unit 13 is transmitted, a determination is made such that a force equivalent to that obtained when the operator 6 directly grips the forceps 2a, 2b is transmitted to the slave control unit 35. When the determination flag is "1", an influence of the abdominal wall 3 is eliminated to make it possible to make a determination so as to transmit only forces acting on the tip ends of the forceps 2a and 2b to the slave control units 35, respectively.

Next, in step S203, smoothing is performed onto information of a force to be transmitted to the slave control unit 35 by the force correction unit 41 such that the force set before the switching is smoothly switched to the force set after the switching to prevent a force from being quickly changed when the determination flags are switched in the force transmitting portion determination unit 36. Force information obtained after smoothing is output to be transmitted from the force transmitting portion determination unit 36 to the slave control unit 35.

Next, in step 204, the force information output to the slave control unit 35 is sent to the master control unit 28 and transmitted to the force transmitting unit 27. The force information input to the force transmitting unit 27 is transmitted to a hand of the operator 6.

Effects of Third Embodiment

As described above, according to instructions from the operator 6 to the master robot 18, when the forceps 2a, 2b are to be inserted by the slave robot 19 from outside the body toward an affected area such as a brain or a heart of the human body 4, transmissions of a force equivalent to that generated when the operator 6 in a conventional technique directly grips the forceps 2a, 2b and only a force acting on the tip end of the forceps 2a, 2b can be switched by the force transmitting portion determination unit 36. Thus, the force generated when the operator 6 in the conventional technique directly grips the forceps 2a, 2b can be felt in the former, and only the forces at the tip ends of the forceps 2a, 2b can be transmitted regardless of a force acting on the abdominal wall 3 in the latter.

Fourth Embodiment

In a fourth embodiment, as in the third embodiment, as shown in FIG. 19, a case in which the forceps 2a, 2b are inserted into a body through the use of a master-slave device 100D will be exemplified. As the fourth embodiment, the descriptions of the same parts as those in the first, second, and the third embodiments are omitted, and only different parts will be described below in detail.

First, an outline of the master-slave device 100D according to the fourth embodiment of the present invention will be described below with reference to FIG. 19 used in the third embodiment. A configuration shown in FIG. 19 in the third embodiment is the same as that in the fourth embodiment, and only the internal configurations of the master robots 25 and the slave robots 26 are different.

While the operator 6 operates the master robot 25 to insert the forceps 2a, 2b into the body, forces generated when the forceps 2a, 2b act on the abdominal wall 3 or forces generated when the tip ends of the forceps 2a, 2b on the inner side of the body act on the internal organ are individually measured by the force measurement apparatuses 1a and 1b, respectively. When it is decided that a load is applied, in addition to a warning made through the monitor 17a or the loudspeaker 17b, the control of the slave is stopped by the slave robot 26.

Furthermore, the operator 6, as in the third embodiment, can give instructions for a forceps operation while checking a video image of an endoscope displayed on the monitor 17a or a warning or the like from the force measurement apparatuses 1a and 1b. The start and end instructions of force measurement of the force measurement apparatus 1 are given in conjunction with the start and the stop instructions of an inserting task of the slave robot 26 through operating the master robot 25.

Figure 22:
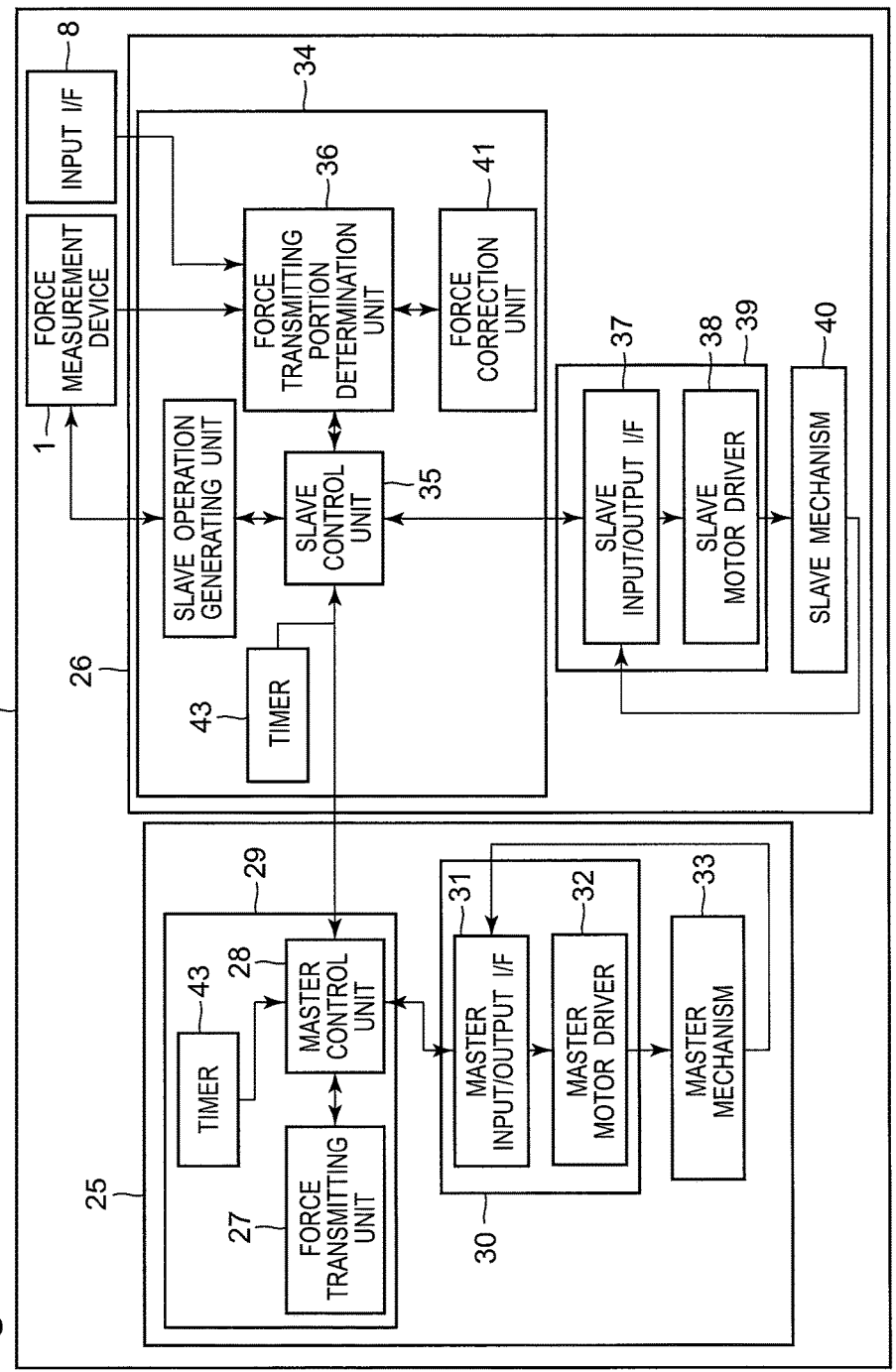
FIG. 22 is a block diagram showing a detailed configuration of a master-slave device according to a fourth embodiment of the present invention.

Next, details of the force measurement apparatuses 1a, 1b, the master robot 25, and the slave robot 26 according to the fourth embodiment will be described below. FIG. 22 is a block diagram of the force measurement apparatus 1, the master robot 25, and the slave robot 26. The descriptions of the parts common in the fourth and third embodiments are omitted, and only parts different from those in the third embodiment will be described below.

<<Slave Mechanism 40>>

The slave mechanism 40 is a robot that inserts the forceps 2a, 2b into a body. The slave mechanism 40 operates so as to follow the position information acquired by the master mechanism 33, and operates by an operation generated by a slave operation generating unit 35 (will be described later).

<<Slave Control Device 34>>

The slave control device 34 includes the slave control unit 35, the force transmitting portion determination unit 36, the timer 43, and the force correction unit 41 as in the third embodiment, and further includes a slave operation generating unit 42. The slave control device 34 has three roles. The first role is to cause the slave mechanism 40 to follow position information from the master control device 29. The second role is to determine a force transmitted to the master control device in a force transmitting portion determination unit 36 based on the force information acquired in the force measurement apparatus 1, correct the determined force by the force correction unit 41, and output the corrected force to the master control device 29 as force information. The third role is to perform control based on an operation generated by the slave operation generating unit 42. Each of the force measurement apparatuses 1 (1a, 1b), as shown in FIG. 19, is disposed on the tip end side of the forceps 2a, 2b and outside the body near a position where the slave robot 19 is disposed.

<<Slave Operation Generating Unit 42>>

When the force decision unit 12 decides that force information is a threshold value for deciding load or more and that a load is applied to the living body 4, the slave operation generating unit 42 generates an operation to stop the slave operation performed by the slave mechanism 40. More specifically, the slave operation generating unit 42 generates an operation to stop a slave operation based on force information or a load decision result acquired by each of the force measurement apparatuses 1. When the force decision unit 12 of the force measurement apparatus 1 decides that a load is applied, the slave operation generating unit 42 outputs instructions to the slave control unit 35 to stop the slave operation.

An operating procedure of the master-slave device 100D according to the fourth embodiment will be described below with reference to the flow chart in FIG. 23.

Figure 23:
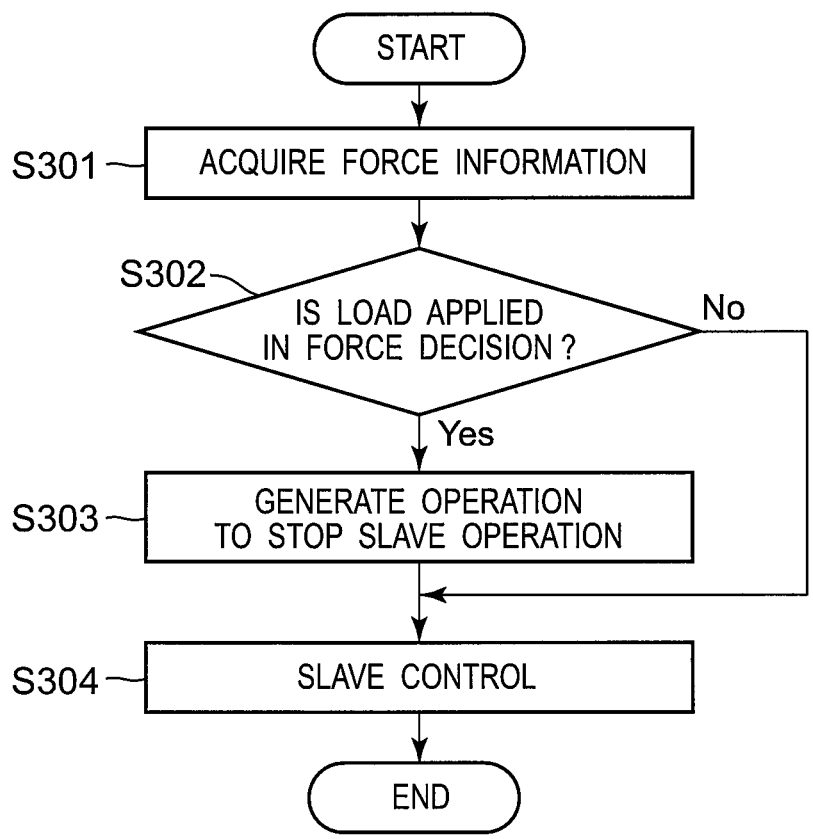
FIG. 23 is a flow chart of an operating procedure of the master-slave device according to the fourth embodiment of the present invention.

In FIG. 23, in a case where the operator 6 directly touches the master mechanism 33 to operate the slave mechanism 40 that inserts the forceps 2a, 2b into a body, a control procedure of the slave mechanism 40 when the forceps 2a, 2b are brought into contact with the human body 4 will be described.

In step S301, in a case where the tip ends of the forceps 2a, 2b on the inner side of the body are brought into contact with the internal organ 5 when the forceps 2a, 2b are inserted into the body, force information is detected by the force measurement apparatus 1 and the force detection unit 13 and output to a slave operation generating unit 42.

Next, in step S302, the slave operation generating unit 42 detects whether the force decision unit 12 of the force measurement apparatus 1 decides that a load is applied.

When the force decision unit 12 of the force measurement apparatus 1 decides in step S302 that a load is applied, the control procedure proceeds to step S303 to cause the slave operation generating unit 42 to output instructions to the slave control unit to stop the slave operation. On the other hand, when the force decision unit of the force measurement apparatus 1 decides in step S302 that a load is not applied, the control procedure proceeds to step S304.

In step 304, the slave mechanism 40 is controlled by instructions from the slave operation generating unit 42.

Effects of Fourth Embodiment

As described above, when the force decision unit 12 decides that a load is applied to the living body 4, in addition to a warning made by the operator 6 through a monitor 8a or a loudspeaker 8b, the control of the slave is stopped by the slave robot 26. For this reason, the living body 4 can be prevented from being hurt any more.

(Modification)

In the first embodiment, an example in which a force acts on the forceps 2a, 2b as shown in FIG. 12C in a z-axis direction, and in an x-axis direction as shown in FIG. 17A in the second embodiment is exemplified. However, also when the forceps 2a, 2b are inserted to be inclined in a direction having a sign different from that of the x-axis direction or a y-axis direction, the force can be measured by the same method as described above.

In the first embodiment, as shown in FIGS. 10A to 10E, reference information in a plurality of directions is generated by performing an actual operation. However, for example, when reference information is generated in a positive x-axis direction, reference information in a negative x-axis direction may be generated by inverting the signs.

The reference information generating unit 15 or the calculation unit 11a of the individual force calculation unit 11 automatically calculates a reference point by a displacement of force. However, for example, the operator 6 may set a reference point through the input IF 8 such that a time point at which the forceps passes through the abdominal wall 3 is set as the reference point.

The reference information obtained before the correction is replaced for correction by the reference information correction unit 23. However, the reference information that is previously generated may be left, and reference information that is newly corrected may be added.

Furthermore, in the embodiment, forces in only the insertion direction of the forceps 2a, 2b are described. However, forces in directions perpendicular to the insertion direction may be measured by the same method as described above.

In the embodiment, individual forces are calculated at two positions, i.e., the abdominal wall 3 and the internal organ. However, the region of the abdominal wall 3 may be divided to calculate individual forces at two or more portions.

In this specification, as an example of a region except for a region to be measured, the abdominal wall 3 serving as a wall separating an inside of body from an outside of body is described as a typical example. However, the present disclosure is not limited to the abdominal wall 3. Alternatively, the body wall such as a chest wall may be used. In short, the wall merely means a portion that separates the inside of body including a region to be measured such as a treated region including a surgery site or an examination region, from the outside of body. For example, when the region to be measured is a liver, a region except for the region to be measured includes an abdominal wall including skin and fat.

In exchange of the instruments, reference information may be always generated again. Alternatively, when an instrument is similar, the reference information that has been generated may be used. At this time, when pieces of identification information of an instrument are included in the reference information database 22 or the like of the force measurement apparatus 1 disposed in the instrument, the pieces of identification information are compared with each other to make it possible to automatically decide the necessity of generation of reference information in step S2.

Though the present disclosure has been described above based on the above first to third embodiments, the present disclosure should not be limited to the above-described first to third embodiments. For example, the present disclosure also includes the following cases.

Part or entirety of each of the above-described apparatuses is actually a computer system that includes, for example, a microprocessor, ROM, RAM, hard disk unit, display unit, keyboard, mouse, and the like. A computer program is stored on the RAM or the hard disk unit. Functions of each unit of the apparatuses can be achieved by the microprocessor operating according to the computer program. The computer program mentioned here is a combination of a plurality of instruction codes that indicate commands to a computer for achieving predetermined functions.

For example, each component can be implemented as a result that a program executing unit such as a CPU reads and executes software programs recorded in a recording medium such as a hard disk or semiconductor memory. Here, software that implements a part or entirety of the constituent units of the force measurement apparatus(es) according to the above embodiment(s) or modification(s) is a following program. That is to say, this program is a force measurement program for measuring a force generated, in endoscopic surgery in which an operator inserts an instrument into a body of a living body, when the instrument inserted into the body is brought into contact with the living body, the force measurement program causing a computer to execute steps of:

causing a force detection unit disposed outside the living body to detect a force generated when the instrument having a tip end inserted into the body of the living body acts on the living body;

causing a reference information generating unit to, when the tip end of the instrument is inserted from outside of the living body into the body toward a region to be measured in the body and reaches the region to be measured through a region except for the region to be measured, generate reference information serving as information relating to a force acting on the region except for the region to be measured; and causing an individual force calculation unit to, when the instrument is inserted into the body of the living body, individually calculate forces generated when the instrument acts on the region to be measured in the body based on information of the force detected by the force detection unit and the reference information generated by the reference information generating unit.

In addition, it may be possible to execute the program by downloading it from a server or reading it from a predetermined storage medium (an optical disc such as a CD-ROM, a magnetic disc, a semiconductor memory, or the like).

Further, one or more computers can be used to execute the program. That is, centralized processing or distributed processing can be performed.

By properly combining the arbitrary embodiment(s) or modification(s) of the aforementioned various embodiments and modifications, the effects possessed by the embodiment(s) or modification(s) can be produced.

The entire disclosure of Japanese Patent Application No. 2012-273684 filed on Dec. 14, 2012, including specification, claims, drawings, and summary are incorporated herein by reference in its entirety.

A force measurement apparatus, a force measurement method, a force measurement program, a force measurement integrated electronic circuit, and a master-slave device according to the present invention are useful as a force measurement apparatus, a force measurement method, a force measurement program, and a force measurement integrated electronic circuit that measure a force when a forceps is inserted into a living body. Furthermore, the master-slave device according to the present invention is useful as a master-slave device using the force measurement apparatus.

Although the present invention has been fully described in connection with the embodiments thereof with reference to the accompanying drawings, it is to be noted that various changes and modifications are apparent to those skilled in the art. Such changes and modifications are to be understood as included within the scope of the present invention as defined by the appended claims unless they depart therefrom.

What is claimed is:

1. A force measurement apparatus that measures a first force generated during endoscopic surgery by an instrument that is configured to be inserted into a body by an operator, when the instrument, when inserted into the body, is brought into contact with the body, the force measurement apparatus comprising:

a force detection sensor that is mounted on a portion of the instrument, such that when a tip end of the instrument is inserted into the body, the portion of the instrument on which the force detection sensor is mounted is outside the body, wherein the force detection sensor detects a second force generated when the instrument, having the tip end inserted into the body, acts on the body;

a position measurement sensor that is mounted on a portion of the instrument and that acquires a position or an orientation of the instrument inserted into the body, a processor; and a non-transitory computer-readable recording medium having executable instructions stored thereon, which when executed by the processor, cause the force measurement apparatus to:

when the tip end of the instrument is inserted from outside of the body into the body toward a region to be measured in the body and reaches the region to be measured through a region except for the region to be measured, generate reference information based on the second force detected by the force detection sensor and the position or the orientation of the instrument acquired by the position measurement sensor, wherein the reference information is information is configured by pairing the position or the orientation of the instrument and the second force detected by the force detection sensor with time in a state in which the tip end of the instrument is inserted into the body and is not in contact with the region to be measured, wherein the reference information includes at least two directions intersecting with a direction in which the instrument is inserted into the body and information of displacement of a time-series of the second force detected by the force detection sensor in the directions, and wherein when the instrument is inserted into the body, the executable instructions, when executed by the processor, further cause the force measurement apparatus to set, based on the reference information, (i) a first time point at which the displacement of the second force detected by the force detection sensor changes by a predetermined threshold value for setting the first time point or more and (ii) a second time point at which displacement of the second force detected by the force detection sensor changes by a predetermined threshold value for setting the second time point or more;

sequentially search the reference information for a position close to a position of the instrument at the second time point from the first time point;

select the reference information including in a matched position obtained by the searching; and individually calculate the first force by subtracting (i) a third force acting on the region except for the region to be measured, the third force being calculated from the selected reference information from (ii) the second force detected by the force detection sensor, the first force being generated when the instrument acts on the region to be measured in the body.

2. The force measurement apparatus according to claim 1, wherein the region to be measured is a region to be examined in the body or a region to be treated, including a surgery site, and the region except for the region to be measured is skin, a body wall, or fat.

3. The force measurement apparatus according to claim 1, wherein the executable instructions, when executed by the processor, further cause the force measurement apparatus to decide, when the reference information is not selected, that the reference information needs to be corrected and then perform notification to the operator that the reference information needs to be corrected.

4. The force measurement apparatus according to claim 1, wherein the executable instructions, when executed by the processor, further cause the force measurement apparatus to decide, when the second force detected by the force detection sensor or the individually calculated first force is a predetermined threshold value for deciding a load or more, that a load is applied to a region in the body.

5. The force measurement apparatus according to claim 1, wherein the executable instructions, when executed by the processor, further cause the force measurement apparatus to display the second force detected by the force detection sensor, the individually calculated first force, or a decided decision result such that the second force detected by the force detection sensor, the individually calculated first force, or the decided decision result is added to an image obtained by capturing the body.

6. The force measurement apparatus according to claim 1, wherein the executable instructions, when executed by the processor, further cause the force measurement apparatus to provide notification to the operator of the second force detected by the force detection sensor, the individually calculated first force, or a decided decision result, through voice.

7. A force measurement method for measuring a first force generated during endoscopic surgery by an instrument that is configured to be inserted into a body by an operator, when the instrument, when inserted into the body, is brought into contact with the body, the force measurement method comprising:
    detecting, with a force detection sensor, a second force generated when the instrument, having a tip end inserted into the body, acts on the body, the force detection sensor being mounted on the instrument at a portion of the instrument that is outside the body when the tip end is inserted into the body;
    acquiring, with a position measurement sensor, a position or an orientation of the instrument inserted into the body, the position measurement sensor being mounted on a portion of the instrument; and
    when the tip end of the instrument is inserted from outside of the body into the body toward a region to be measured in the body and reaches the region to be measured through a region except for the region to be measured, generating reference information based on the second force detected by the force detection sensor and the position or the orientation of the instrument acquired by the position measurement sensor,
    wherein the reference information is information is configured by pairing the position or the orientation of the instrument and the second force detected by the force detection sensor with time in a state in which the tip end of the instrument is inserted into the body and is not in contact with the region to be measured,
    wherein the reference information includes at least two directions intersecting with a direction in which the instrument is inserted into the body and information of displacement of a time-series of the second force detected by the force detection sensor in the directions, and
    wherein when the instrument is inserted into the body, the force measurement method further comprises:
        setting, based on the reference information, (i) a first time point at which the displacement of the second force detected by the force detection sensor changes by a predetermined threshold value for setting the first time point or more and (ii) a second time point at which displacement of the second force detected by the force detection sensor changes by a predetermined threshold value for setting the second time point or more;
        sequentially searching the reference information for a position close to a position of the instrument at the second time point from the first time point;
        selecting the reference information including in a matched position obtained by the searching; and
        individually calculating the first force by subtracting (i) a third force acting on the region except for the region to be measured, the third force being calculated from the selected reference information from (ii) the second force detected by the force detection sensor, the first force being generated when the instrument acts on the region to be measured in the body.

8. A non-transitory computer-readable recording medium including a force measurement program for measuring a first force generated during endoscopic surgery by an instrument that is configured to be inserted into a body by an operator, when the instrument, when inserted into the body, is brought into contact with the body, the force measurement program causing a computer to execute steps of:
    detecting, with a force detection sensor, a second force generated when the instrument, having a tip end inserted into the body, acts on the body, the force detection sensor being mounted on the instrument at a portion of the instrument that is outside the body when the tip end is inserted into the body;
    acquiring, with a position measurement sensor, a position or an orientation of the instrument inserted into the body, the position measurement sensor being mounted on a portion of the instrument; and
    when the tip end of the instrument is inserted from outside of the body into the body toward a region to be measured in the body and reaches the region to be measured through a region except for the region to be measured, generating reference information based on the second force detected by the force detection sensor and the position or the orientation of the instrument acquired by the position measurement sensor,
    wherein the reference information is information is configured by pairing the position or the orientation of the instrument and the second force detected by the force detection sensor with time in a state in which the tip end of the instrument is inserted into the body and is not in contact with the region to be measured,
    wherein the reference information includes at least two directions intersecting with a direction in which the instrument is inserted into the body and information of displacement of a time-series of the second force detected by the force detection sensor in the directions, and
    wherein when the instrument is inserted into the body, the force measurement method further comprises:

setting, based on the reference information, (i) a first time point at which the displacement of the second force detected by the force detection sensor changes by a predetermined threshold value for setting the first time point or more and (ii) a second time point at which displacement of the second force detected by the force detection sensor changes by a predetermined threshold value for setting the second time point or more;

sequentially searching the reference information for a position close to a position of the instrument at the second time point from the first time point;

selecting the reference information including in a matched position obtained by the searching; and individually calculating the first force by subtracting (i) a third force acting on the region except for the region to be measured, the third force being calculated from the selected reference information from (ii) the second force detected by the force detection sensor, the first force being generated when the instrument acts on the region to be measured in the body.

9. A force measurement integrated electronic circuit that measures a first force generated during endoscopic surgery by an instrument that is configured to be inserted into a body by an operator, when the instrument, when inserted into the body, is brought into contact with the body, the force measurement integrated electronic circuit comprising:

a force detection circuit that is mounted on a portion of the instrument, such that when a tip end of the instrument is inserted into the body, the portion of the instrument on which the force detection circuit is mounted is outside the body, wherein the force detection circuit detects a second force generated when the instrument, having the tip end inserted into the body, acts on the body;

a position measurement sensor that is mounted on a portion of the instrument and that acquires a position or an orientation of the instrument inserted into the body; and a reference information generating circuit that, when the tip end of the instrument is inserted from outside of the body into the body toward a region to be measured in the body and reaches the region to be measured through a region except for the region to be measured, generates reference information based on the second force detected by the force detection sensor and the position or the orientation of the instrument acquired by the position measurement sensor wherein the reference information is information is configured by pairing the position or the orientation of the instrument and the second force detected by the force detection sensor with time in a state in which the tip end of the instrument is inserted into the body and is not in contact with the region to be measured, wherein the reference information includes at least two directions intersecting with a direction in which the instrument is inserted into the body and information of displacement of a time-series of the second force detected by the force detection sensor in the directions, and wherein the force measurement integrated electronic circuit further comprises an individual force calculation circuit that, when the instrument is inserted into the body:

sets, based on the reference information, (i) a first time point at which the displacement of the second force detected by the force detection sensor changes by a predetermined threshold value for setting the first time point or more and (ii) a second time point at which displacement of the second force detected by the force detection sensor changes by a predetermined threshold value for setting the second time point or more;

sequentially searches the reference information for a position close to a position of the instrument at the second time point from the first time point;

selects the reference information including in a matched position obtained by the searching; and individually calculates the first force by subtracting (i) a third force acting on the region except for the region to be measured, the third force being calculated from the selected reference information from (ii) the second force detected by the force detection sensor, the first force being generated when the instrument acts on the region to be measured in the body.

10. A master-slave device that includes a slave mechanism that is configured to insert an instrument into a body during endoscopic surgery and a master mechanism that is configured to be operated by an operator so as to remote-control the slave mechanism, the master-slave device comprising a force measurement apparatus disposed in the instrument outside the body, the force measurement apparatus comprising:

a force detection sensor that is mounted on a portion of the instrument, such that when a tip end of the instrument is inserted into the body, the portion of the instrument on which the force detection sensor is mounted is outside the body, wherein the force detection sensor detects a second force generated when the instrument, having the tip end inserted into the body, acts on the body;

a position measurement sensor that is mounted on a portion of the instrument and that acquires a position or an orientation of the instrument inserted into the body;

a first processor; and a first non-transitory computer-readable recording medium having first executable instructions stored thereon, which when executed by the first processor, cause the force measurement apparatus to:

generate, when the tip end of the instrument is inserted from outside of the body into the body toward a region to be measured in the body and reaches the region to be measured through a region except for the region to be measured, reference information based on the second force detected by the force detection sensor and the position or the orientation of the instrument acquired by the position measurement sensor, wherein the reference information is information is configured by pairing the position or the orientation of the instrument and the second force detected by the force detection sensor with time in a state in which the tip end of the instrument is inserted into the body and is not in contact with the region to be measured, wherein the reference information includes at least two directions intersecting with a direction in which the instrument is inserted into the body and information of displacement of a time-series of the second force detected by the force detection sensor in the directions, and wherein when the instrument is inserted into the body, the first executable instructions, when executed by the first processor, further cause the force measurement apparatus to
- set, based on the reference information, (i) a first time point at which the displacement of the second force detected by the force detection sensor changes by a predetermined threshold value for setting the first time point or more and (ii) a second time point at which displacement of the second force detected by the force detection sensor changes by a predetermined threshold value for setting the second time point or more;
- sequentially search the reference information for a position close to a position of the instrument at the second time point from the first time point;
- select the reference information including in a matched position obtained by the searching; and
- individually calculate a first force by subtracting (i) a third force acting on the region except for the region to be measured, the third force being calculated from the selected reference information from (ii) the second force detected by the force detection sensor, the first force being generated when the instrument acts on the region to be measured in the body, wherein the master-slave device further comprises:
a second processor; and
a second non-transitory computer-readable recording medium having second executable instructions stored thereon, which when executed by the second processor, cause the master slave device to:
- determine and correct a fourth force transmitted from the slave mechanism to the master mechanism based on information of the individually calculated first force;
- transmit information of the corrected fourth force to the master mechanism;
- convert, when the master mechanism is operated by the operator based on the information of the corrected fourth force, operation information of the master mechanism into an electric signal; and
- output a control signal that transmits the operation information of the master mechanism to the slave mechanism, wherein based on the transmitted control signal, the slave mechanism is operated to perform a slave operation.

11. The master-slave device according to claim 10, wherein the first executable instructions, when executed by the first processor, further cause the force measurement apparatus to:
- decide that a load is applied to the body when information of the individually calculated first force is a predetermined threshold value for deciding a load or more,
- the second executable instructions, when executed by the second processor, cause the master-slave device to further: generate an operation to stop a slave operation by the slave mechanism when the force information is decided to be the predetermined threshold for deciding the load or more and that the load is applied to the body, and
- control the slave mechanism based on the generated operation.

* * * * *